US007129221B2

(12) United States Patent
Or et al.

(10) Patent No.: US 7,129,221 B2
(45) Date of Patent: Oct. 31, 2006

(54) 6,11-BICYCLIC ERYTHROMYCIN DERIVATIVES

(75) Inventors: Yat Sun Or, Watertown, MA (US); Guoqiang Wang, Belmont, MA (US); Ly Tam Phan, Malden, MA (US); Deqiang Niu, Lexington, MA (US); Yao-Ling Qiu, Andover, MA (US); Nha Huu Vo, Southborough, MA (US); Jay Judson Farmer, New Haven, CT (US); Ying Hou, Everett, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 642 days.

(21) Appl. No.: 10/436,622

(22) Filed: May 13, 2003

(65) Prior Publication Data
US 2004/0053861 A1 Mar. 18, 2004

Related U.S. Application Data

(63) Continuation-in-part of application No. 10/144,396, filed on May 13, 2002, now abandoned.

(51) Int. Cl.
*A61K 31/7048* (2006.01)
*A61K 31/7052* (2006.01)
*C07H 17/08* (2006.01)
(52) U.S. Cl. .................... 514/28; 536/17.4; 536/7.1
(58) Field of Classification Search ............. 514/28; 536/17.4, 7.1
See application file for complete search history.

(56) References Cited

U.S. PATENT DOCUMENTS

| 4,990,602 | A | 2/1991 | Morimoto et al. ........... 536/7.4 |
| 5,403,923 | A | 4/1995 | Kashimura et al. .......... 536/7.4 |
| 5,444,051 | A | 8/1995 | Agouridas et al. ............ 514/29 |
| 5,527,780 | A | 6/1996 | Agouridas et al. ............ 514/29 |
| 5,631,355 | A | 5/1997 | Asaka et al. ................. 536/7.4 |
| 5,866,549 | A | 2/1999 | Or et al. ........................ 514/29 |
| 5,969,161 | A | 10/1999 | Bonnet et al. ............... 549/271 |
| 6,046,171 | A | 4/2000 | Or et al. ........................ 514/29 |
| 6,124,269 | A | 9/2000 | Phan et al. ................... 514/29 |
| 6,399,582 | B1 | 6/2002 | Hlasta et al. ................. 514/29 |
| 6,878,691 | B1* | 4/2005 | Or et al. ........................ 514/29 |

FOREIGN PATENT DOCUMENTS

WO    WO 99 21864    5/1999

OTHER PUBLICATIONS

U.S. Appl. No. 10/429,485, filed May 5, 2003, Or et al.
International Search Report of International Application No. PCT/US 03/14914, Applicant: Enanta Pharmaceuticals, Inc.; Applicant's File Reference ENP-034 PCT, Jul. 30, 2003.

* cited by examiner

*Primary Examiner*—James O. Wilson
*Assistant Examiner*—Ganapathy Krishnan
(74) *Attorney, Agent, or Firm*—Elmore, Craig & Vanstone, P.C.; Darlene A. Vanstone; Carolyn S. Elmore

(57) ABSTRACT

The present invention discloses compounds of formula I, or pharmaceutically acceptable salts, esters, or prodrugs thereof:

(I)

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

35 Claims, No Drawings

6,11-BICYCLIC ERYTHROMYCIN DERIVATIVES

REFERENCE TO RELATED APPLICATIONS

This application is a continuation in part of prior U.S. patent application Ser. No. 10/144,396, filed May 13, 2002 now abandoned.

TECHNICAL FIELD

The present invention relates to novel semisynthetic macrolides having antibacterial activity and useful in the treatment and prevention of bacterial infections. More particularly, the invention relates to 6,11-3-carbon bridged erythromcyin derivatives, compositions containing such compounds and methods for using the same, as well as processes for making such compounds.

BACKGROUND OF THE INVENTION

Erythromycins A through D, represented by formula (E) as illustrated below,

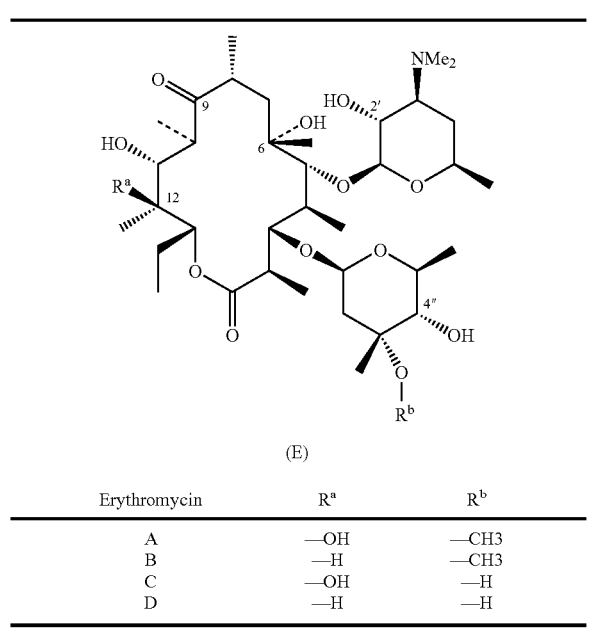

(E)

| Erythromycin | $R^a$ | $R^b$ |
|---|---|---|
| A | —OH | —CH3 |
| B | —H | —CH3 |
| C | —OH | —H |
| D | —H | —H | are well-known and potent antibacterial agents, used widely to treat and prevent bacterial infection. As with other antibacterials, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Kashimura et al. have disclosed 6-O-methylerythromycin derivatives having a tricyclic basic nuclear structure in European Application 559896, published Nov. 11, 1991.

Also, Asaka et al. have disclosed 5-O-desosminylerythronolide derivatives containing a tricyclic carbamate structure in PCT Application WO 93/21200, published Apr. 22, 1992.

Recently erythromycin derivatives containing a variety of substituents at the 6-O position have been disclosed in U.S. Pat. Nos. 5,866,549, 6,075,011 and 6,420,555 B1 as well as PCT Applications WO 00/78773 and WO 03/024986. Furthermore, Ma et. al. have described erythromycin derivatives with aryl groups tethered to the C-6 position in *J. Med Chem.*, 44, pp 4137–4156 (2001).

SUMMARY OF THE INVENTION

The present invention provides a novel class of C6–C11 bridged erythromycin compounds that possess antibacterial activity.

In one aspect of the present invention there are disclosed novel bridged erythromycin compounds represented by formula I as illustrated below:

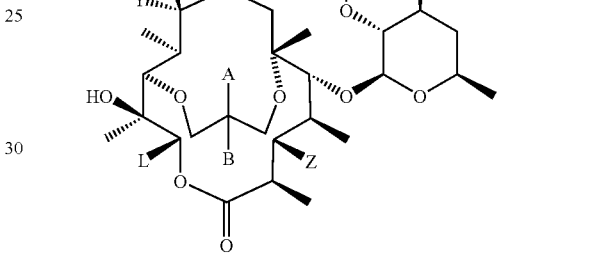

(I)

as well as its pharmaceutically acceptable salts, esters and prodrugs, wherein
A is selected from:
  a) —OH;
  b) —OR$_p$, where R$_p$ is a hydroxy protecting group;
  c) —R$_1$, where R$_1$ is independently selected from:
    (1) aryl;
    (2) substituted aryl;
    (3) heteroaryl; and
    (4) substituted heteroaryl;
  d) —OR$_1$, where R$_1$ is as previously defined;
  e) —R$_2$, where R$_2$ is selected from:
    (1) hydrogen;
    (2) halogen;
    (3) $C_1$–$C_{12}$ alkyl optionally containing 0, 1, 2, or 3 heteroatoms selected from O, S or N, optionally substituted with one or more substituents selected from halogen, aryl, substituted aryl, heteroaryl, and substituted heteroaryl;
    (4) $C_2$–$C_{12}$ alkenyl optionally containing 0, 1, 2, or 3 heteroatoms selected from O, S and N, optionally substituted with one or more substituents selected from halogen, aryl, substituted aryl, heteroaryl, and substituted heteroaryl; and
    (5) $C_2$–$C_{12}$ alkynyl optionally containing 0, 1, 2, or 3 heteroatoms selected from O, S and N, optionally substituted with one or more substituents selected from halogen, aryl, substituted aryl, heteroaryl, and substituted heteroaryl;

f) —OR$_2$, where R$_2$ is independently previously defined;
g) —S(O)$_n$R$_{11}$, where n=0, 1 or 2, and R$_{11}$ is independently hydrogen, R$_1$ or R$_2$, where R$_1$ and R$_2$ are as previously defined;
h) —NHC(O)R$_{11}$, where R$_{11}$ is as previously defined;
i) —NHC(O)NHR$_{11}$, where R$_{11}$ is as previously defined;
j) —NHS(O)$_2$R$_{11}$, where R$_{11}$ is as previously defined;
k) NR$_{14}$R$_{15}$, where R$_{14}$ and R$_{15}$ are each independently R$_{11}$, where R$_{11}$ is as previously defined; and
l) —NHR$_3$, where R$_3$ is an amino protecting group;

B is selected from:
a) hydrogen;
b) deuterium;
c) halogen
d) —OH;
e) —R$_1$, where R$_1$ is as previously defined;
f) —R$_2$, where R$_2$ is as previously defined; and
g) —OR$_p$, where R$_p$ is as previously defined, provided that when B is halogen, —OH, or —OR$_p$, A is R$_1$ or R$_2$;

or alternatively, A and B taken together with the carbon atom to which they are attached are selected from:
a) C=O;
b) C(OR$_2$)$_2$, where R$_2$ is as previously defined;
c) C(SR$_2$)$_2$, where R$_2$ is as previously defined;
d) C(OR$_{12}$)(OR$_{13}$), where R$_{12}$ and R$_{13}$ are independently C$_1$–C$_6$ alkyl or taken together are —(CH$_2$)$_m$—, where m=2 or 3;
e) C(SR$_{12}$)(SR$_{13}$), where R$_{12}$, R$_{13}$, and m are as previously defined;
f) C=CHR$_{11}$, where R$_{11}$ is as previously defined;
g) C=N—O—R$_{11}$, where R$_{11}$ is as previously defined;
h) C=N—O-Ar$_1$-M-Ar$_2$, wherein
  (1) -Ar$_1$- is R$_{31}$, where R$_{31}$ is independently selected from:
    (a) —R$_1$, where R$_1$ is as previously defined;
    (b) —C$_1$–C$_{12}$ alkyl optionally containing 0, 1, 2, or 3 heteroatoms selected from O, S or N, optionally substituted with one or more substituents selected from halogen, aryl, substituted aryl, heteroaryl, and substituted heteroaryl;
    (c) —C$_2$–C$_{12}$ alkenyl optionally containing 0, 1, 2, or 3 heteroatoms selected from O, S and N, optionally substituted with one or more substituents selected from halogen, aryl, substituted aryl, heteroaryl, and substituted heteroaryl; or
    (d) —C$_2$–C$_{12}$ alkynyl optionally containing 0, 1, 2, or 3 heteroatoms selected from O, S and N, optionally substituted with one or more substituents selected from halogen, aryl, substituted aryl, heteroaryl, and substituted heteroaryl;
  (2) -M- is absent or selected from:
    (a) —C$_1$–C$_{12}$ alkyl optionally containing:
      1. 0–3 heteroatoms selected from O, S or N; and
      2. 0–3 groups selected from —C=N—, —N=N— or C(O);
    (b) —C$_2$–C$_{12}$ alkenyl optionally containing:
      1. 0–3 heteroatoms selected from O, S or N; and
      2. 0–3 groups selected from —C=N—, —N=N—, or C(O);
    (c) —C$_2$–C$_{12}$ alkynyl optionally containing:
      1. 0–3 heteroatoms selected from O, S or N; and
      2. 0–3 groups selected from —C=N—, —N=N—, or C(O);
    (d) substituted aryl;
    (e) substituted heteroaryl; or
    (f) substituted heterocycloalkyl; and
  (3) -Ar$_2$ is selected from:
    (a) aryl;
    (b) substituted aryl;
    (c) heteroaryl; or
    (d) substituted heteroaryl;
i) C=NNHR$_{11}$, where R$_{11}$ is as previously defined;
j) C=NNHC(O)R$_{11}$, where R$_{11}$ is as previously defined;
k) C=NNHC(O)NHR$_{11}$, where R$_{11}$ is as previously defined;
l) C=NNHS(O)$_2$R$_{11}$, where R$_{11}$ is as previously defined;
m) C=NNHR$_3$, where R$_3$ is as previously defined;
n) C=NR$_{11}$, where R$_{11}$ is as previously defined; or
o) C=N—N=CHR$_{11}$, where R$_{11}$ is as previously defined;

one of X and Y is hydrogen and the other is selected from:
a) hydrogen;
b) deuterium;
c) —OH;
d) —OR$_p$, where R$_p$ is as previously defined;
e) —NR$_4$R$_5$, where R$_4$ and R$_5$ are each independently selected from:
  (1) hydrogen;
  (2) C$_1$–C$_{12}$ alkyl, optionally substituted with one or more substituents selected from halogen, aryl, substituted aryl, heteroaryl and substituted heteroaryl; or
  (3) R$_4$ and R$_5$, taken together with the nitrogen atom to which they are attached form a 3–10 membered heteroalkyl ring containing 0–2 additional hetero atoms selected from O, S, and N; or alternatively, X and Y taken together with the carbon atom to which they are attached are selected from:
a) C=O;
b) C=N—Q, wherein Q is selected from:
  (1) R$_{11}$, where R$_{11}$ is as previously defined;
  (2) amino protecting group;
  (3) C(O)R$_{11}$, where R$_{11}$ is as previously defined; or
  (4) OR$_6$, where R$_6$ is independently selected from:
    (a) hydrogen;
    (b) —CH$_2$O(CH$_2$)$_2$OCH$_3$,
    (c) —CH$_2$O(CH$_2$O)$_n$CH$_3$, where n is as previously defined;
    (d) —C$_1$–C$_{12}$ alkyl, optionally substituted with one or more substituents selected from aryl, substituted aryl, heteroaryl and substituted heteroaryl;
    (e) C$_3$–C$_{12}$ cycloalkyl;
    (f) C(O)—C$_1$–C$_{12}$ alkyl;
    (g) C(O)—C$_3$–C$_{12}$ cycloalkyl;
    (h) C(O)—R$_{11}$, where R$_{11}$ is as previously defined; or
    (i) —Si(R$_a$)(R$_b$)(R$_c$), wherein R$_a$, R$_b$ and R$_c$ are each independently selected from C$_1$–C$_{12}$ alkyl, aryl, and substituted aryl; or
  (5) O—C(R$_7$)(R$_8$)—O—R$_6$, where R$_6$ is as previously defined, provided that R$_6$ is not C(O)—C$_1$–C$_{12}$ alkyl, C(O)—C$_3$–C$_{12}$ cycloalkyl, or C(O)—R$_1$, and R$_7$ and R$_8$ taken together with the carbon atom to which they are attached form a C$_3$–C$_{12}$ cycloalkyl group or each independently is selected from:
    1. hydrogen; or
    2. C$_1$–C$_{12}$ alkyl;

L is selected from:
b) —CH$_3$;
c) —CH$_2$CH$_3$;
d) —CH(OH)CH$_3$;

e) C$_1$–C$_6$ alkyl, optionally substituted with one or more substituents selected from aryl, substituted aryl, heteroaryl, and substituted heteroaryl;

f) C$_2$–C$_6$ alkenyl, optionally substituted with one or more substituents selected from aryl, substituted aryl, heteroaryl, and substituted heteroaryl; or g) C$_2$–C$_6$ alkynyl, optionally substituted with one or more substituents selected from aryl, substituted aryl, heteroaryl, and substituted heteroaryl;

W is —NR$_{14}$R$_{15}$, where R$_{15}$ and R$_{15}$ are each independently selected from:
a) hydrogen;
b) C$_1$–C$_{12}$ alkyl, optionally substituted with one or more substituents selected from halogen, aryl, substituted aryl, heteroaryl and substituted heteroaryl;
c) C$_2$–C$_{12}$ alkenyl, optionally substituted with one or more substituents selected from halogen, aryl, substituted aryl, heteroaryl and substituted heteroaryl;
d) C$_2$–C$_{12}$ alkynyl, optionally substituted with one or more substituents selected from halogen, aryl, substituted aryl, heteroaryl and substituted heteroaryl; or
e) R$_{14}$ and R$_{15}$, taken together with the nitrogen atom to which they are attached form a heterocycloalkyl cyclic moiety;

Z is selected from:
(a) hydrogen;
(b) —OH;
(c) —OR$_p$, where R$_p$ is as previously defined;
(d) —OR$_{11}$, where R$_{11}$ is as previously defined;
(e) —OC(O)R$_{11}$, where R$_{11}$ is as previously defined;
(f) —OC(O)NHR$_{11}$, where R$_{11}$ is as previously defined;
(g) —S(O)$_n$R$_{11}$, where n and R$_{11}$ are as previously defined; or
(h) —

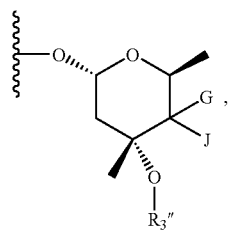

where
i. R$_3$" is hydrogen or methyl; and
ii. where one of J or G is hydrogen, the other is selected from:
1. hydrogen;
2. deuterium;
3. —OH;
4. —OR$_p$, where R$_p$ is previously defined;
5. —OR$_4$", where R$_4$" is hydrogen or R$_p$, where R$_p$ is as previously defined; or
6. —NR$_4$R$_5$, where R$_4$ and R$_5$ is as previously defined; or
iii. in the alternative, J and G are taken together with the carbon atom to which they are attached to form a group selected from:
1. C=O;
2. C=N—Q, wherein Q is as previously defined; and R$_2$' is hydrogen or R$_p$, where R$_p$, is as previously defined.

In another embodiment of the present invention there are disclosed pharmaceutical compositions comprising a therapeutically effective amount of any compound of the present invention in combination with a pharmaceutically acceptable carrier or excipient. In yet another embodiment of the invention are methods of treating antibacterial infections in a subject with said pharmaceutical compositions. Suitable carriers and methods of formulation are also disclosed.

In a further aspect of the present invention there are provided processes for the preparation of 6,11-3C-bridged erythromycin derivatives of formula (I) via any synthetic route delineated herein.

DETAILED DESCRIPTION OF THE INVENTION

A first embodiment of the present invention is a compound of formula I as defined herein, or its pharmaceutically acceptable salt, ester, or prodrug.

Representative subgenera of the present invention are:

A compound according to claim 1, which is represented by formula II:

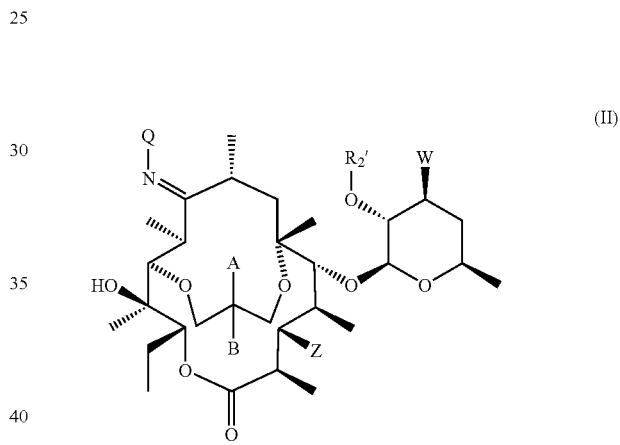

where A, B, Q, R$_2$', W, and Z are as previously defined;

A compound according to claim 1, which is represented by formula III:

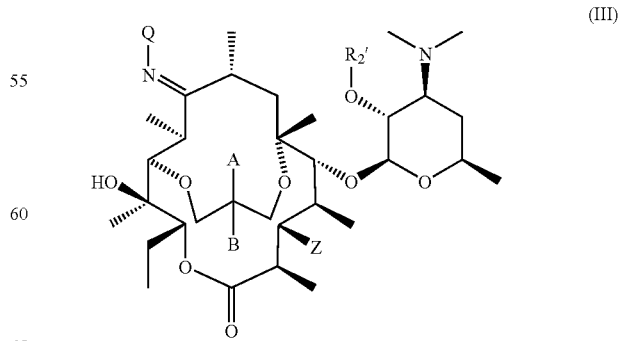

where A, B, Q, R$_2$', and Z are as previously defined;

A compound according to claim 1, which is represented by formula IV:

(IV)

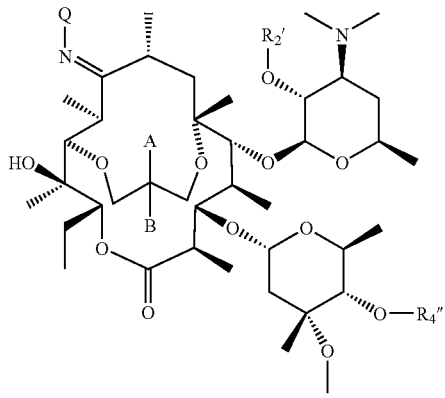

where A, B, Q, $R_2'$, and $R_4''$ are as previously defined;

A compound according to claim 1, which is represented by formula V:

(V)

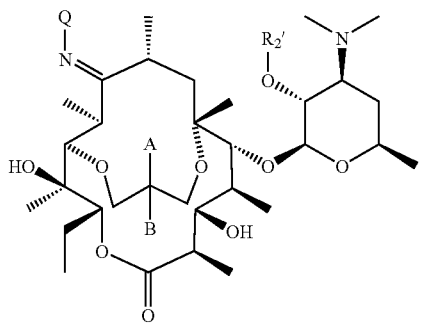

where A, B, Q, and $R_2'$ are as previously defined;

A compound according to claim 1, which is represented by formula VI:

(VI)

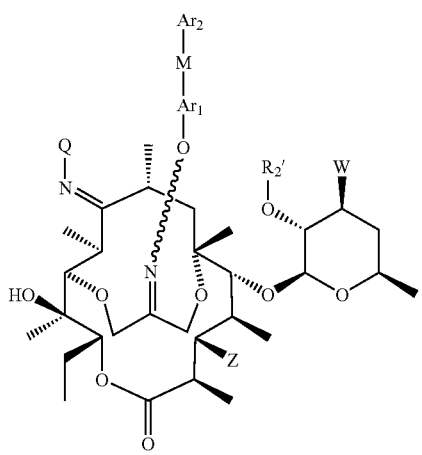

where $Ar_1$, $Ar_2$, M, Q, $R_2'$, W, and Z are as previously defined;

A compound according to claim 1, which is represented by formula VII:

(VII)

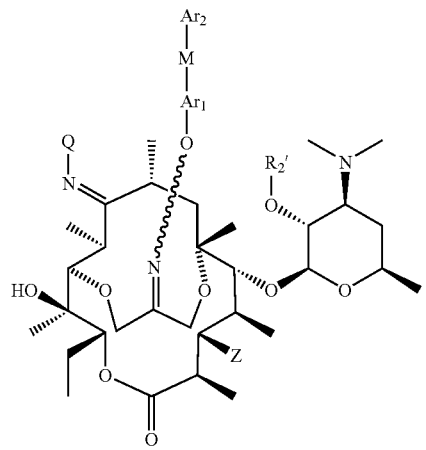

where $Ar_1$, $Ar_2$, M, Q, $R_2'$, and Z are as previously defined;

A compound according to claim 1, which is represented by formula VIII:

(VIII)

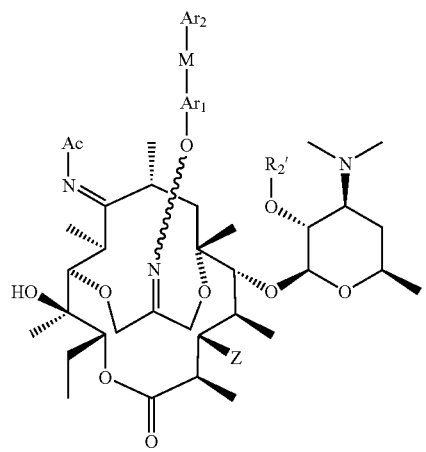

where $Ar_1$, $Ar_2$, M, $R_2'$, and Z are as previously defined;

A compound according to claim 1, which is represented by formula IX:

(IX)

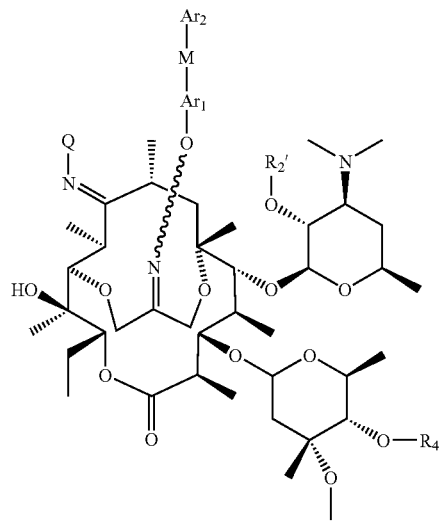

where $Ar_1$, $Ar_2$, M, Q, $R_2'$, and $R_4''$ are as previously defined; and

A compound according to claim 1, which is represented by formula X:

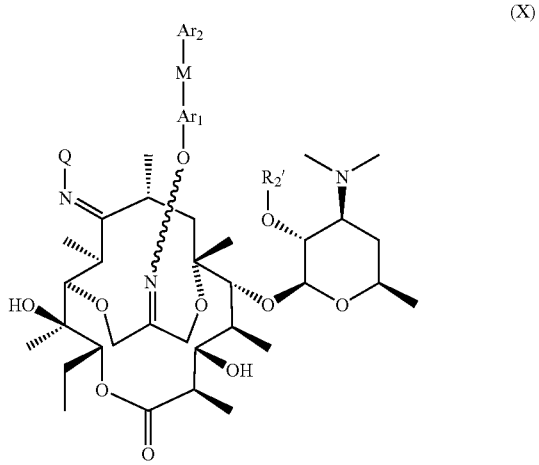

where $Ar_1$, $Ar_2$, M, Q, and $R_2'$ are as previously defined.

Representative compounds according to the invention are those selected from:

1) Compound of formula IV: A and B taken together with the carbon atom to which they are attached=C═$CH_2$, Q=OH, $R_2'$ is H, and $R_4''$=Ac;
2) Compound of formula IV: A and B taken together with the carbon atom to which are attached=C═$CH_2$, Q=H, $R_2$=H, and $R_4''$=Ac;
3) Compound of formula V: A and B taken together with the carbon atom to which they are attached=C═$CH_2$, Q=H, and $R_2'$=H;
4) Compound of formula V: A and B taken together with the carbon atom to which they are attached=C═$CH_2$, Q=Ac, and $R_2'$=H;
5) Compound of formula IV: A and B taken together with the carbon atom to which they are attached=C═$CH_2$, Q=O—$CH_2OCH_3$, $R_2'$=H, and $R_4''$=Ac;
6) Compound of formula V: A and B taken together with the carbon atom to which they are attached=C═$CH_2$, Q=O—CH2$OCH_3$, and $R_2'$=H;
7) Compound of formula I: A and B taken together with the carbon atom to which they are attached=C═$CH_2$, X and Y taken together with the carbon atom to which they are attached=C═NAc, L=$CH_2CH_3$, W is $N(CH_3)_2$, Z=H and $R_2'$=H;
8) Compound of formula I: A and B taken together with the carbon atom to which they are attached=C═CH2, X and Y taken together with the carbon atom to which they are attached=C═NAc, L=$CH_2CH_3$, Z=OC(O)(p-nitrophenyl) and $R_2'$=H;
9) Compound of formula I: A and B taken together with the carbon atom to which they are attached=C═$CH_2$, X and Y taken together with the carbon atom to which they are attached=C═NAc, L=$CH_2CH_3$, W is $N(CH_3)_2$, Z=OC(O)[2-($NO_2$), 4-($CF_3$)Phenyl] and $R_2'$=H;
10) Compound of formula I: A and B taken together with the carbon atom to which they are attached=C═$CH_2$, X and Y taken together with the carbon atom to which they are attached=C═NAc, L=$CH_2CH_3$, W is $N(CH_3)_2$, Z=OC(O)$CH_2$(p-methoxyphenyl) and $R_2'$=H;
11) Compound of formula IV: A and B taken together with the carbon atom to which they are attached=C═$CH_2$, Q=Ac, $R_2'$=H, and $R_4''$=Ac;
12) Compound of formula I: Compound of formula IV: A and B taken together with the carbon atom to which they are attached=C═O, Q=Ac, $R_2'$=H, and $R_4''$=Ac;
13) Compound of formula IV: A and B taken together with the carbon atom to which they are attached=C═OBz, Q=Ac, $R_2'$=H, and $R_4''$=Ac;
14) Compound of formula IV: A and B taken together with the carbon atom to which they are attached=C═(3-quinolyl), Q=Ac, $R_2'$=H, and $R_4''$=Ac;
15) Compound of formula I: A and B taken together with the carbon atom to which they are attached=C═$CH_2$, X and Y taken together with the carbon atom to which they are attached=C═O, L=$CH_2CH_3$, W is $N(CH_3)_2$, Z=4-acetoxycladinose and $R_2'$=H;
16) Compound of formula I: A and B taken together with the carbon atom to which they are attached=C═CH-quinolin-3-yl, X and Y taken together with the carbon atom to which they are attached=C═O, L=$CH_2CH_3$, W is $N(CH_3)_2$, Z=4-acetoxycladinose and $R_2'$=H;
17) Compound of formula I: A and B taken together with the carbon atom to which they are attached=C═CH-quinolin-3-yl, X and Y taken together with the carbon atom to which they are attached=C═O, L=$CH_2CH_3$, W is $N(CH_3)_2$, Z=OH, and $R_2'$=H;
18) Compound of formula I: A and B taken together with the carbon atom to which they are attached=C═$CH_2$, X and Y taken together with the carbon atom to which they are attached=C═O, L=$CH_2CH_3$, W is $N(CH_3)_2$, Z=OH and $R_2'$=H;
19) Compound of formula IV: A and B taken together with the carbon atom to which they are attached=C═$CH_2$-phenyl, Q=OH, $R_2'$=H, and $R_4''$=Ac;
20) Compound of formula V: A and B taken together with the carbon atom to which they are attached are C═CH-phenyl, Q=Ac, and $R_2'$=H;
21) Compound of formula I: A and B taken together with the carbon atom to which they are attached=C═O, X and Y taken together with the carbon atom to which they are attached=C═NAc, L=$CH_2CH_3$, W is $N(CH_3)_2$, Z=$OCH_2$CH═CH(quinolin-3-yl), and $R_2'$=H;
22) Compound of formula I: A and B taken together with the carbon atom to which they are attached=C═CHCHCH-phenyl, X and Y taken together with the carbon atom to which they are attached=C═NAc, L=$CH_2CH_3$, W is $N(CH_3)_2$, Z=OC(O)-benzyl and $R_2'$=H;
23) Compound of formula I: A and B taken together with the carbon atom to which they are attached=C═CHCHCH-phenyl, X and Y taken together with the carbon atom to which they are attached=C═NAc, L=$CH_2CH_3$, W is $N(CH_3)_2$, Z=OC(O)$CH_2$(2-pyridyl) and $R_2'$=H;
24) Compound of formula I: A and B taken together with the carbon atom to which they are attached=C═$CH_2$, X and Y taken together with the carbon atom to which they are attached=C═NOH, L=$CH_2CH_3$, W is $N(CH_3)_2$, Z=4-oxocladinose and $R_2'$=H;
25) Compound of formula I: A and B taken together with the carbon atom to which they are attached=C═$CH_2$, X and Y taken together with the carbon atom to which they are attached=C=NOH, L=CH$_2$CH$_3$, W is N(CH$_3$)$_2$, Z=4-oximecladinose and R$_2$'=H;

26) Compound of formula IV: A and B taken together with the carbon atom to which they are attached are C=CH$_2$, Q=OH, and R$_2$'=R$_4$"=H;

27) Compound of formula I: Compound of formula IV: A and B taken together with the carbon atom to which they are attached=C=CH$_2$, Q=OH, R$_2$'=H, and R$_4$"=Ac.

In another aspect, the present invention relates to a method for controlling a bacterial infection in a subject (e.g., mammal, human, horse, dog, cat, fish) comprising administering to the subject a therapeutically effective amount of a pharmaceutical composition described herein. The method includes administering to the subject (including a subject identified as in need of such treatment) a therapeutically effective amount of any compound delineated herein, or any pharmaceutical composition delineated herein to produce such effect.

Yet another aspect of this invention relates to a method of treating a subject (e.g., mammal, human, horse, dog, cat, fish) having bacterial infection or disease or disease symptom related to having a bacterial infection (including diseases delineated herein). The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Also within the scope of this invention is a packaged product. The packaged product includes a container, one of the aforementioned compounds in the container, and a legend (e.g., a label or an insert) associated with the container and indicating administration of the compound for treating a disorder associated with bacterial infection, including the diseases delineated herein.

In a further aspect of the present invention is a process of making any compound delineated herein via any synthetic route delineated herein.

Definitions

Listed below are definitions of various terms used to describe this invention. These definitions apply to the terms as they are used throughout this specification and claims, unless otherwise limited in specific instances, either individually or as part of a larger group.

The terms "C$_1$–C$_3$ alkyl," "C$_1$–C$_6$ alkyl," or "C$_1$–C$_{12}$ alkyl," as used herein, refer to saturated, straight- or branched-chain hydrocarbon radicals containing between one and three, one and twelve, or one and six carbon atoms, respectively. Examples of C$_1$–C$_3$ alkyl radicals include methyl, ethyl, propyl and isopropyl radicals; examples of C$_1$–C$_6$ alkyl radicals include, but are not limited to, methyl, ethyl, propyl, isopropyl, n-butyl, tert-butyl, neopentyl and n-hexyl radicals; and examples of C$_1$–C$_{12}$ alkyl radicals include, but are not limited to, ethyl, propyl, isopropyl, n-hexyl, octyl, decyl, dodecyl radicals.

The term "substituted alkyl," as used herein, refers to a "C$_2$–C$_{12}$ alkyl" or "C$_1$–C$_6$ alkyl" group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroaryl amino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkenyl, —S(O)—C$_3$–C$_{12}$-cycloalkyl, —S(O)-aryl, —S(O)-heteroaryl, —S(O)-heterocycloalkyl—SO$_2$NH$_2$, —SO$_2$NH—C$_1$–C$_{12}$-alkyl, —SO$_2$NH—C$_2$–C$_{12}$-alkenyl, —SO$_2$NH—C$_2$–C$_{12}$-alkenyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkenyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, -methoxymethoxy, -methoxyethoxy, —SH, —S—C$_1$–C$_{12}$-alkyl, —S—C$_2$–C$_{12}$-alkenyl, —S—C$_2$–C$_{12}$-alkenyl, —S—C$_3$–C$_{12}$-cycloalkyl, —S-aryl, —S-heteroaryl, —S-heterocycloalkyl, or methylthiomethyl.

The terms "C$_2$–C$_{12}$ alkenyl" or "C$_2$–C$_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The term "substituted alkenyl," as used herein, refers to a "$C_2$–$C_{12}$ alkenyl" or "$C_2$–$C_6$ alkenyl" group as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkeny, —$NHCO_2$—$C_3$–$C_{12}$-cycloalkyl, —$NHCO_2$-aryl, —$NHCO_2$-heteroaryl, —$NHCO_2$-heterocycloalkyl, —$NHC(O)NH_2$, $NHC(O)NH$—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, $NHC(S)NH_2$, $NHC(S)NH$—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —$NHC(NH)NH_2$, $NHC(NH)NH$—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, $NHC(NH)$—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3C_{12}$-cycloalkyl, —$SO_2NH$-aryl, —$SO_2NH$-heteroaryl, —$SO_2NH$-heterocycloal kyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The terms "$C_2$–$C_{12}$ alkynyl" or "$C_2$–$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$–$C_{12}$ alkynyl" or "$C_2$–$C_6$ alkynyl" group as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_2$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —$NHC(O)NH_2$, $NHC(O)NH$—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, $NHC(S)NH_2$, $NHC(S)NH$—$C_1$–$C_{12}$-alkyl, —NHC(S)NH—$C_2$–$C_2$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —$NHC(NH)NH_2$, $NHC(NH)NH$—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, $NHC(NH)$—$C_1$–$C_{12}$-alkyl, —NHC(NH)—$C_2$–$C_{12}$-alkenyl, —NHC(NH)—$C_2$–$C_{12}$-alkenyl, —NHC(NH)-$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)

NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —$SO_2NH_2$, —$SO_2NH$—$C_1$–$C_{12}$-alkyl, —$SO_2NH$—$C_2$–$C_{12}$-alkenyl, —$SO_2NH$—$C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH —$C_1$–$C_{12}$-alkyl, —NH— $C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH— $C_1$–$C_{12}$-alkyl, —CONH—$C_2$–$C_{12}$-alkenyl, —CONH— $C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{C12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH— $C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$–$C_{12}$-alkyl, —NHC(S)NH— $C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)— $C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl—$SO_2NH_2$, —$SO_2NH$— $C_1$–$C_{12}$-alkyl, —$SO_2NH$—$C_2$–$C_{12}$-alkenyl, —$SO_2NH$— $C_2$–$C_{12}$-alkenyl, —$SO_2NH$—$C_3$–$C_{12}$-cycloalkyl, —$SO_2NH$-aryl, —$SO_2NH$-heteroaryl, —$SO_2NH$-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "arylalkyl," as used herein, refers to a $C_1$–$C_3$ alkyl or $C_1$–$C_6$ alkyl residue attached to an aryl ring. Examples include, but are not limited to, benzyl, phenethyl and the like.

The term "substituted arylalkyl," as used herein, refers to an arylalkyl group, as previously defined, substituted by independent replacement or one, two, or three of the hydrogen atoms thereon with substituents including, but not limited to, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH— $C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)— $C_2$–$C_{12}$-alkenyl, —C(O)—$C_2$–$C_{12}$-alkenyl, —C(O)— $C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkenyl, —S(O)-C$_3$–C$_{12}$-cycloalkyl, —S(O)-aryl, —S(O)-heteroaryl, —S(O)-heterocycloalkyl—SO$_2$NH$_2$, —SO$_2$NH—C$_1$–C$_{12}$-alkyl, —SO$_2$NH—C$_2$–C$_{12}$-alkenyl, —SO$_2$NH—C$_2$–C$_{12}$-alkenyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkenyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, -methoxymethoxy, -methoxyethoxy, —SH, —S—C$_1$–C$_{12}$-alkyl, —S—C$_2$–C$_{12}$-alkenyl, —S—C$_2$–C$_{12}$-alkenyl, —S—C$_3$–C$_{12}$-cycloalkyl, —S-aryl, —S-heteroaryl, —S-heterocycloalkyl, or methylthiomethyl.

The term "heteroaryl," as used herein, refers to a mono-, bi-, or tri-cyclic aromatic radical or ring having from five to ten ring atoms of which one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "substituted heteroaryl," as used herein, refers to a heteroaryl group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, -OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkenyl, —S(O)—C$_3$–C$_{12}$-cycloalkyl, —S(O)-aryl, —S(O)-heteroaryl, —S(O)-heterocycloalkyl—SO$_2$NH$_2$, —SO$_2$NH—C$_1$–C$_{12}$-alkyl, —SO$_2$NH—C$_2$–C$_{12}$-alkenyl, —SO$_2$NH—C$_2$–C$_{12}$-alkenyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkenyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, -methoxymethoxy, -methoxyethoxy, —SH, —S—C$_1$–C$_{12}$-alkyl, —S—C$_2$–C$_{12}$-alkenyl, —S—C$_2$–C$_{12}$-alkenyl, —S—C$_3$–C$_2$-cycloalkyl, —S-aryl, —S-heteroaryl, —S-heterocycloalkyl, or methylthiomethyl.

The term "C$_3$–C$_{12}$-cycloalkyl," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl.

The term "substituted C$_3$–C$_{12}$-cycloalkyl," as used herein, refers to a C$_3$–C$_{12}$-cycloalkyl group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkenyl, —S(O)—C$_3$–C$_{12}$-cycloalkyl, —S(O)-aryl, —S(O)-heteroaryl, —S(O)-heterocycloalkyl—SO$_2$NH$_2$, —SO$_2$NH—C$_1$–C$_{12}$-alkyl, —SO$_2$NH—C$_2$–C$_{12}$-alkenyl, —SO$_2$NH—C$_2$–C$_{12}$-alkenyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkenyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, -methoxymethoxy, -methoxyethoxy, —SH, —S—C$_1$–C$_{12}$-alkyl, —S—C$_2$–C$_{12}$-alkenyl, —S—C$_2$–C$_{12}$-alkenyl, —S—C$_3$–C$_{12}$-cycloalkyl, —S-aryl, —S-heteroaryl, —S-heterocycloalkyl, or methylthiomethyl.

The term "heterocycloalkyl," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl," as used herein, refers to a heterocycloalkyl group, as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC (NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —$SO_2NH_2$, —$SO_2$NH—$C_1$–$C_{12}$-alkyl, —$SO_2$NH—$C_2$–$C_{12}$-alkenyl, —$SO_2$NH—$C_2$–$C_{12}$-alkenyl, —$SO_2$NH—$C_3$–$C_{12}$-cycloalkyl, —$SO_2$NH-aryl, —$SO_2$NH-heteroaryl, —$SO_2$NH-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "heteroarylalkyl," as used herein, refers to a $C_1$–$C_3$ alkyl or $C_1$–$C_6$ alkyl residue residue attached to a heteroaryl ring. Examples include, but are not limited to, pyridinylmethyl, pyrimidinylethyl and the like.

The term "substituted heteroarylalkyl," as used herein, refers to a heteroarylalkyl group, as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —$SO_2NH_2$, —$SO_2$NH—$C_1$–$C_{12}$-alkyl, —$SO_2$NH—$C_2$–$C_{12}$-alkenyl, —$SO_2$NH—$C_2$–$C_{12}$-alkenyl, —$SO_2$NH—$C_3$–$C_{12}$-cycloalkyl, —$SO_2$NH-aryl, —$SO_2$NH-heteroaryl, —$SO_2$NH-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_3$-alkyl-amino," as used herein, refers to one or two $C_1$–$C_3$-alkyl groups, as previously defined, attached to the parent molecular moiety through a nitrogen atom. Examples of $C_1$–$C_3$-alkyl-amino include, but are not limited to, methylamino, dimethylamino, ethylamino, diethylamino, and propylamino.

The term "alkylamino" refers to a group having the structure —NH($C_1$–$C_{12}$ alkyl) where $C_1$–$C_{12}$ alkyl is as previously defined.

The term "dialkylamino" refers to a group having the structure —N($C_1$–$C_{12}$ alkyl) ($C_1$–$C_{12}$ alkyl), where $C_1$–$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$–$C_{12}$ alkyl) or —C(O)N($C_1$–$C_{12}$ alkyl) ($C_1$–$C_{12}$ alkyl), —C(O)$NH_2$, and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis*, 3rd edition, John Wiley & Sons, New York (1999). Examples of hydroxy protecting groups include, but are not limited to, methylthiomethyl, tert-butyl-dimethylsilyl, tert-butyldiphenylsilyl, acyl substituted with an aromatic group and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

"An effective amount," as used herein, refers to an amount of a compound which confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans- isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefitrisk ratio. Pharmaceutically acceptable salts are well known in the art. For example, S. M. Berge, et al. describes pharmaceutically acceptable salts in detail in J. Pharmaceutical Sciences, 66: 1–19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp. *Pseudomonas* spp.; pharynigitis, rheumatic fever, and glomerulonephritis related to infection by *Streptococcus pyogenes*, Groups C and G streptococci, *Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C–F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum,* or *Nesseria gonorrheae*; toxin diseases related to infection by *S. aureus* (food poisoning and Toxic shock syndrome), or Groups *A, S.* and *C streptococci;* ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp. odontogenic infection related to infection by viridans streptococci; persistent cough related to infection by Bordetella pertussis; gas gangrene related to infection by *Clostridium perfringens* or *Bacteroides* spp.; Skin infection by *S. aureus, Propionibacterium acne*; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica., P. multocida, Mycoplasma bovis,* or *Bordetella* spp.; cow enteric disease related to infection by *E. coli* or *protozoa* (i.e., coccidia, cryptosporidia, etc.), dairy cow mastitis related to infection by *S. aureus, S. uberis, S. agalactiae, S. dysgalactiae, Klebsiella* spp., *Corynebacterium,* or *Enterococcus* spp.; swine respiratory disease related to infection by *A. pleuropneumoniae., P. multocida,* or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius, coagulase* neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al.,"The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 µg/ml to about 0.03 µg/ml. The diluted compounds (2 µl/well) were then transferred into sterile, uninoculated CAMHB (0.2 mL) by use of a 96 fixed tip-pipetting station. The inoculum for each bacterial strain was standardized to $5\times10^5$ CFU/mL by optical comparison to a 0.5 McFarland turbidity standard. The plates were inoculated with 10 µl/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 µg/ml to about 0.03 µg/ml.

All in vitro testing follows the guidelines described in the Approved Standards M7-A4 protocol, published by the National Committee for Clinical Laboratory Standards (NCCLS).

Pharmaceutical Compositions.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form.

Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animals by administering to the patient a therapeutically effective amount of a compound of the invention, in such amounts and for such time as is necessary to achieve the desired result.

By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the scheme and the examples that follow are:
Ac for acetyl;
AIBN for azobisisobutyronitrile;
$Bu_3SnH$ for tributyltin hydride;
CDI for carbonyldiimidazole;
dba for dibenzylidene acetone;
dppb for diphenylphosphino butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;
EtOAc for ethyl acetate;
MeOH for methanol;
$NaN(TMS)_2$ for sodium bis(trimethylsilyl)amide;
NMMO for N-methylmorpholine N-oxide;
TEA for triethylamine;
THF for tetrahydrofuran;
TPP or $PPh_3$ for triphenylphosphine;
MOM for methoxymethyl;
Boc for t-butoxycarbonyl;
Bz for benzyl;
Ph for phenyl;
POPd for dihydrogen dichlorobis(di-tert-butylphosphinito-κP)palladate(II);
TBS for tert-butyl dimethylsilyl; or
TMS for trimethylsilyl.

Synthetic Methods

The compounds and processes of the present invention will be better understood in connection with the following synthetic schemes that illustrate the methods by which the compounds of the invention may be prepared.

A preferred intermediate for the preparation of compounds represented by formula I is a compound represented by the formula

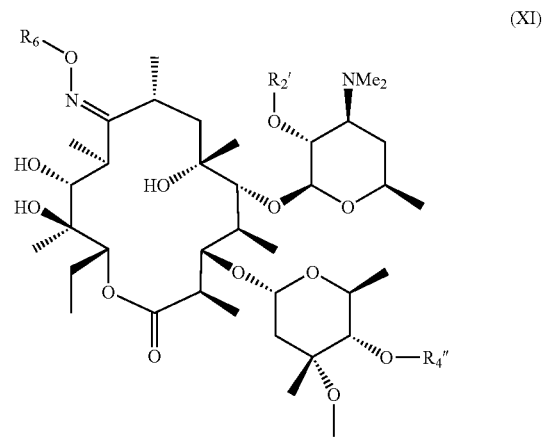

(XI)

where $R_6$, $R_2{}'$ and $R_4{}''$ are as previously defined.

A second preferred intermediate for the preparation of compounds represented by formula I is a compound represented by the formula

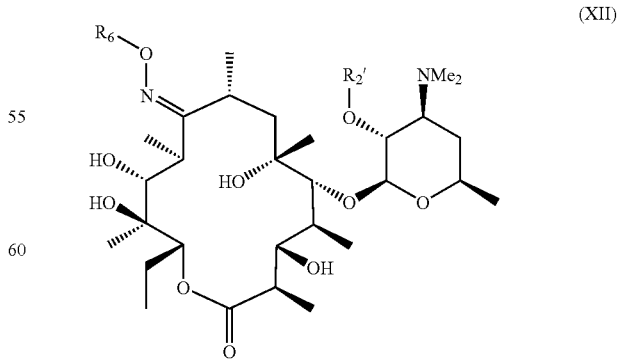

(XII)

where $R_6$ and $R_2{}'$ are as previously defined.

Scheme 1

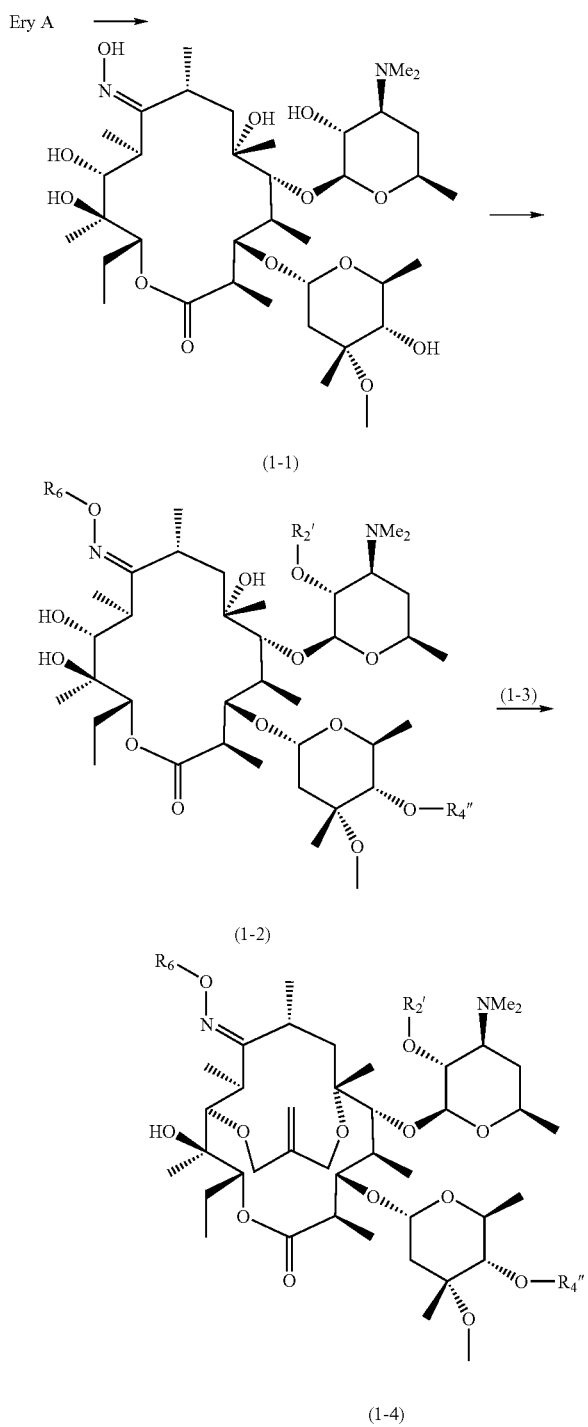

A process of the invention, as illustrated in Scheme 1, involves preparing a compound of formula I (1-4) by reacting a compound of formula (1-2) with a suitable alkylating agent.

In accordance with Scheme 1, the 9-keto group of erythromycins can be initially converted into an oxime by methods described in U.S. Pat. No. 4,990,602, followed by the protection of the 2'- and 4"-hydroxyl and, if desired, the oxime groups of the erythromycin derivatives to obtain the compounds of formula (1-2).

The preparation of protected erythromycins is also described in U.S. Pat. Nos. 4,990,602; 4,331,803; 4,680,386; 4,670,549; or European Patent Application EP 260,938.

The 2'- and 4"-hydroxyl groups are protected by reaction with suitable hydroxyl protecting agents in an aprotic solvent. Typical hydroxyl protecting reagents include, but are not limited to, acetylating agents, silylating agents, acid anhydrides, and the like. Examples of hydroxyl protecting reagents include, but ar not limited to, acetyl chloride, acetic anhydride, benzoyl chloride, benzoic anhydride, benzyl chloroformate, hexamethyldisilazane, and trialkylsilyl chlorides.

Examples of aprotic solvents include, but are not limited to, dichloromethane, chloroform, tetrahydrofuran, N-methylpyrrolidinone, dimethylsulfoxide, N,N-dimethylformamide, N,N-dimethylacetamide, hexamethylphosphoric triaamide, a mixture thereof or a mixture of one of these solvents with ether, tetrahydrofuran, 1,2-dimethoxyethane, 1,2-dichloroethane, acetonitrile, ethyl acetate, acetone and the like. Aprotic solvents do not adversely affect the reaction. Preferably, the solvent is selected from dichloromethane, chloroform, N,N-dimethylformamide, tetrahydrofuran, N-methylpyrrolidinone or mixtures thereof. A more thorough discussion of solvents and conditions for protecting the hydroxyl group can be found in T. W. Greene and P. G. M. Wuts, "Protective Groups in Organic Synthesis" $3^{rd}$ ed., John Wiley & Son, Inc, 1999.

Protection of 2'- and 4"-hydroxyl groups may be accomplished sequentially or simultaneously to provide compound (1-2) where $R_2'$ and/or $R_4''$ can be, for example, acetyl, benzoyl, trimethylsilyl, and the like. Preferred protecting groups include acetyl, benzoyl, and trimethylsilyl. A particularly preferred group for protecting the hydroxyl and oxime groups is the acetyl protecting group, wherein $R_2'=R_4''=R_6=Ac$.

Acetylation of the hydroxyl group is typically accomplished by treating the compound (1-1) with an acetylating reagent, for example, acetic anhydride or acetyl chloride.

The erythromycin derivative of formula (1-1) is then reacted with an alkylating agent of the formula:

(1-3)

where $R_{12}$ is $C_1$–$C_{12}$-alkyl and $R_{11}$ is as previously defined.

Most palladium (0) catalysts are expected to work in this process. Some palladium (II) catalysts, such as palladium (II) acetate, which is converted into a palladium (0) species in-situ by the actions of a phosphine, will work as well. See, for example, Beller et al. *Angew. Chem. Int. Ed. Engl.*, 1995, 34 (17), 1848. The palladium catalyst can be selected from, but not limited to, the group consisting of palladium (II) acetate, tetrakis(triphenylphospine)palladium (0), tris (dibenzylideneacetone)dipalladium, tetradibenzylideneacetone)dipalladium and the like. Palladium on carbon and palladium (II) halide catalysts are less preferred than other palladium catalysts for this process.

Suitable phosphines include, but are not limited to, triphenylphosphine, bis(diphenylphosphino)methane, bis(diphenylphosphino)ethane, bis(diphenylphosphino)propane, 1,4-bis(diphenylphosphino)butane, bis(diphenyl phosphino) pentane, and tri-o-tolyl-phosphine, and the like.

The reaction is carried out in an aprotic solvent, preferably at elevated temperature, preferably at or above 50° C. Suitable aprotic solvents include, but are not limited to, tetrahydrofuran, N,N-dimethylformamide, dimethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. The most preferred solvents are tetrahydrofuran or toluene.

Generally, the alkylating agents have the formula (1-3), previously described. The preferred alkylating agents are those wherein $R_{12}$ is tert-butyl, isopropyl or isobutyl. The alkylating reagents are prepared by reaction of a diol with a wide variety of compounds for incorporating the di-carbonate moiety. The compounds include, but are not limited to, tert-butyl chloroformate, di-tert-butyl dicarbonate, and 1-(tert-butoxycarbonyl)imidazole and the reaction is carried out in the presence of an organic or an inorganic base. The temperature of the reaction varies from about −30° C. to about 30° C. Preferably the alkylating reagent is di-tert-butyl dicarbonate.

An alternative method of converting the alcohol into the carbonate involves treating the alcohol with phosgene or triphosgene to prepare the chloroformate derivative of the diol. The di-chloroformate derivative is then converted into the di-carbonate by the methods described in Cotarca, L., Delogu, P., Nardelli, A., Sunijic, V, *Synthesis*, 1996, 553. The reaction can be carried out in a variety of organic solvents such as dichloromethane, toluene, diethyl ether, ethyl acetate and chloroform in the presence of a base. Examples of suitable bases include, but are not limited to, sodium hydroxide, potassium hydroxide, ammonium hydroxide, sodium carbonate, potassium carbonate, ammonium carbonate,(4-di methylamino)pyridine, pyridine, triethylamine and the like. The temperature can vary from 0° C. to about 60° C. The reaction typically takes about 3 to 5 hours to run to completion.

Another process of the invention involves the removal of the cladinose moiety of the compounds of formula I. The cladinose moiety of the macrolide compound (1-4) is removed either by mild acid hydrolysis or by enzymatic hydrolysis to give compounds of formula (2-1) in Scheme 2. Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol, water and mixtures there of. Reaction times are typically 0.5 to 24 hours. The reaction temperature is preferably 0 to 80° C.

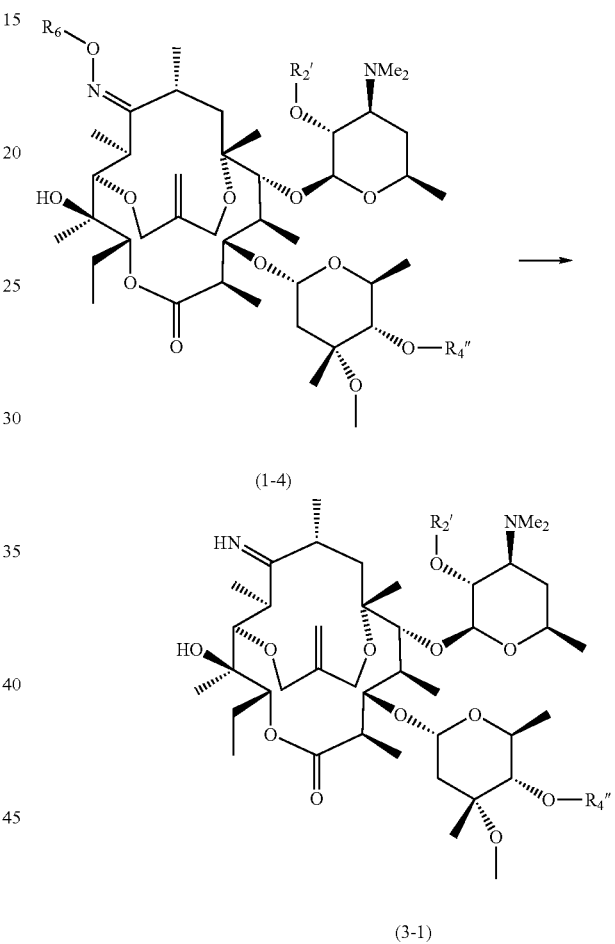

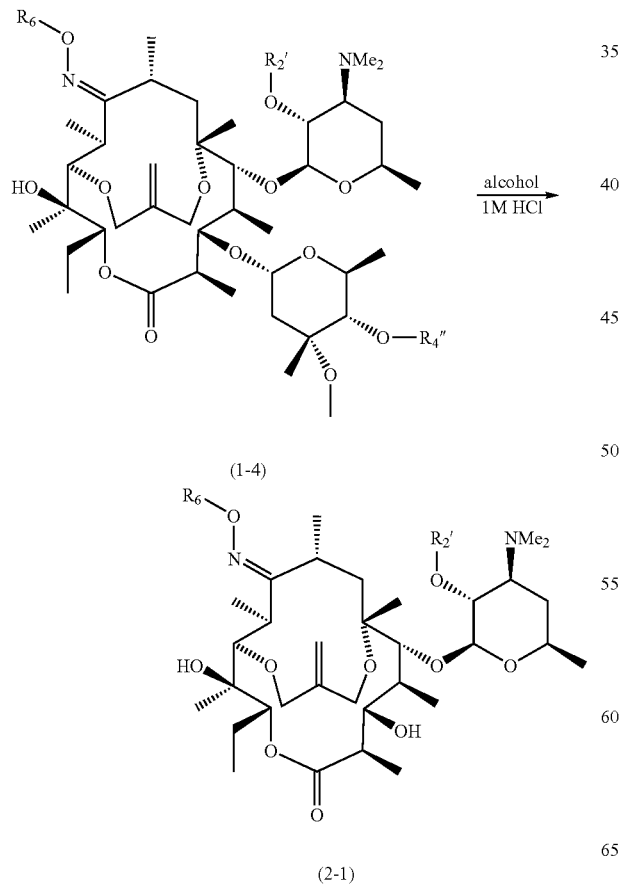

Compounds of formula (1-4) where $R_6$ is Ac can be converted into the corresponding imine as outlined in Scheme 3. Selective deprotection of the oxime is typically accomplished via alkaline hydrolysis in protic solvents. Representative alkali include lithium hydroxide, sodium hydroxide, potassium hydroxide, and the like. Solvents which are applicable include, but are not limited to, tetrahydrofuran, 1,4-dioxane, 1,2-dimethoxyethane, isopropanol, ethanol, butanol, water and mixtures thereof. The reaction temperature is preferably 0° to 35° C. and reaction time is preferably 0.5 to 24 hours.

In a like fashion, simultaneous deprotection of both the oxime and the 2' hydroxyl can be accomplished under a variey of conditions. Conditions for deprotection include, but are not limited to, treating with an alcoholic solvent at from room temperature to reflux, or treatment with a primary amine, such as butylamine. Alcoholic solvents preferred for the deprotection are methanol and ethanol. A more thorough discussion of the procedures, reagents and conditions for removing protecting groups is described in the literature, for example, by T. W. Greene and P. G. M. Wuts in "Protective Groups in Organic Synthesis" $3^{rd}$ ed., John Wiley & Son, Inc, 1999.

Deoxygenation of compounds of formula (1-4) where $R_6$ is H under reducing conditions gives the macrolide imine of formula (3-1). Many reducing agents can be used to effect this transformation including, but not limited to: lithium aluminum hydride, titanium thrichloride, sodium cyanoborohydride, borane, and various sulfides such as sodium hydrogen sulfide, sodium ethoxide. For a more detailed account of oxime reduction see J. March in "Advanced Organic Chemistry" $4^{th}$ ed., Wiley & Son, Inc, 1992, which is incorporated by reference herein.

A particularly useful method for the reduction of oximes to the corresponding imine uses a sulfite reducing agent, such as sodium hydrogensulfite or titanium trichloride under acidic conditions, typically in protic solvents. Representative acids include, but are not limited to, acetic acid, formic acid, dilute hydrochloric acid, dilute phosphoric acid, dilute sulfuric acid, and the like. Protic solvents include, but are not limited to, mixtures of water and methanol, ethanol, isopropanol, or butanol. The reaction is typically carried out at 25° to 110° C., preferably for between 1 and 10 hours.

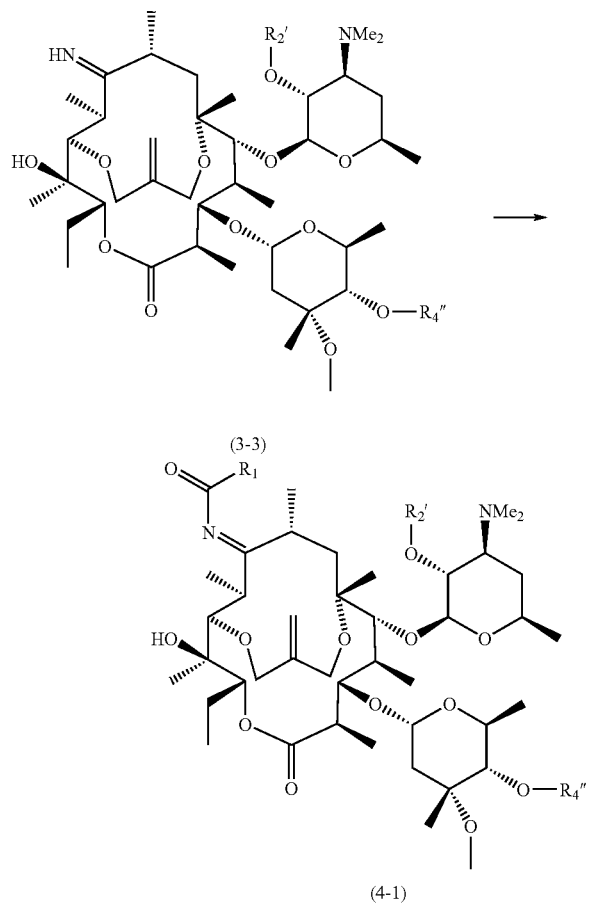

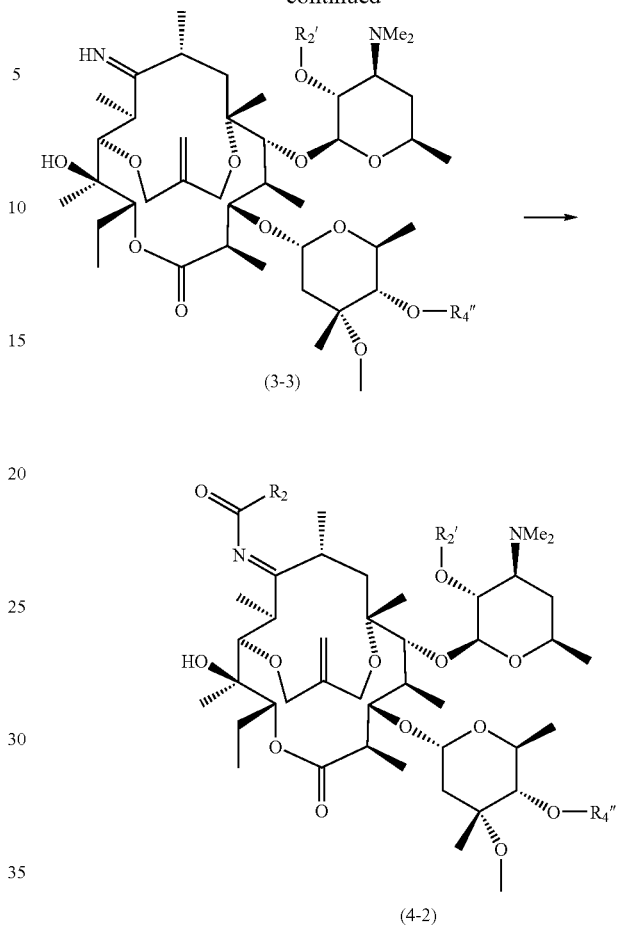

Another process of the invention, as illustrated in Scheme 4, involves a procedure for the acylation of imines of the formula (3-3). The imine is acylated under basic conditions using a suitable acylating agent in an aprotic solvent. Typical acylating agents include, but are not limited to, acid chlorides, acid anhydrides, and chloroformates.

Typical bases include, but are not limited to, pyridine, triethylamine, diisopropyl ethylamine, N-methyl morpholine, N-methyl pyrrolidine, 2,6-lutidine, 1,8-diazabicyclo[5.4.0]undec-7-ene. For a more extensive discourse on acylating conditions see for example, T. W. Greene and P. G. M. Wuts in "Protective Groups in Organic Synthesis" $3^{rd}$ ed., John Wiley & Son, Inc, 1999, referred to above herein.

Conversion of alkene (1-4) into ketone (5-1) can be accomplished by exposure of the alkene to ozone followed by decomposition of the ozonide with the appropriate reducing agent, as outlined in Scheme 5. The reaction is typically carried out in a solvent such as, but not limited to methanol, ethanol, ethyl acetate, glacial acetic acid, chloroform, methylene chloride or hexanes, preferably methanol, preferably at −20° to −78° C. Representative reducing agents are, for example, triphenylphosphine, trimethyl phosphite, thiourea, and dimethyl sulfide, preferably triphenylphosphine. A more thorough discussion of ozonolysis and the conditions there for can be found in J. March "Advanced Organic Chemistry" 4th ed., Wiley & Son, Inc, 1992.

Scheme 5

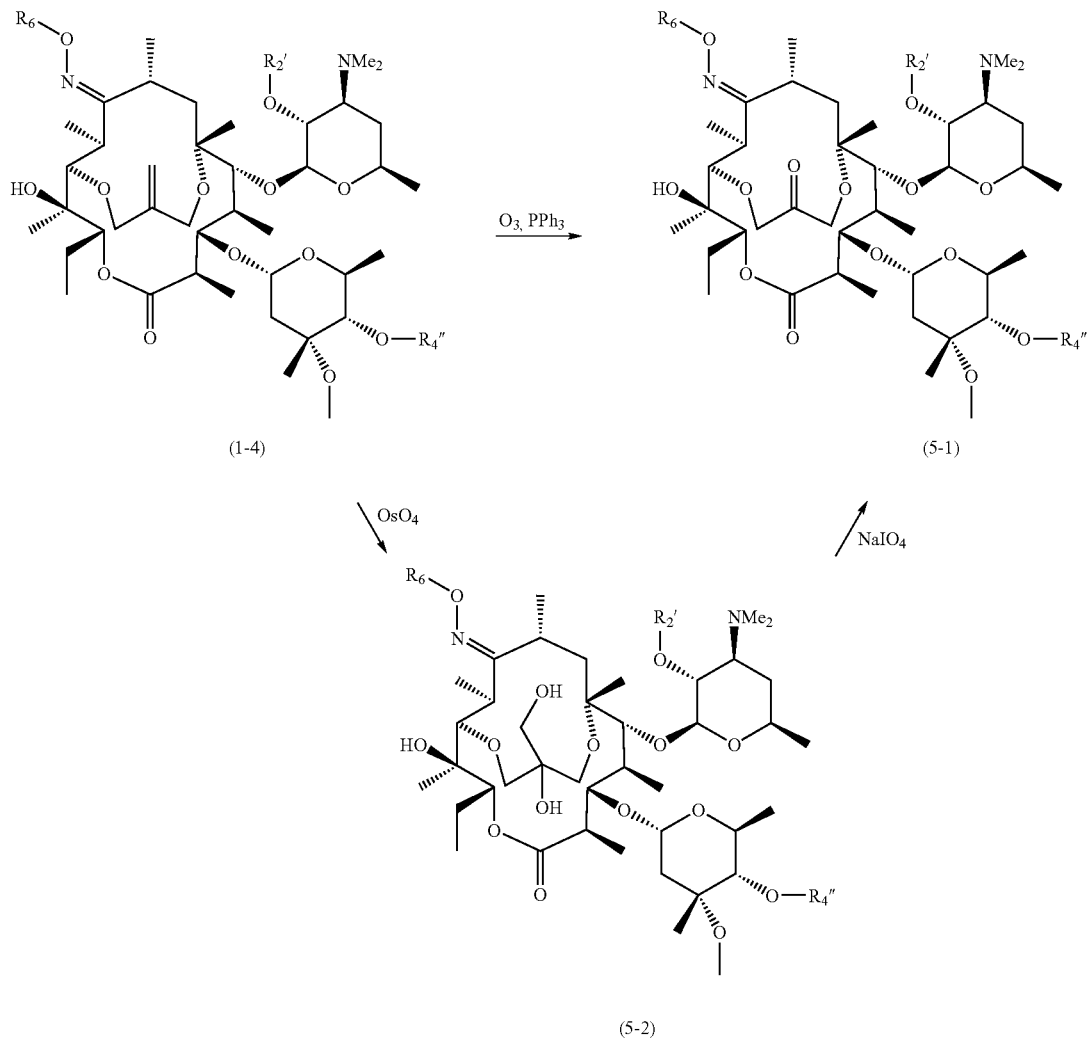

An alternative method for the preparation of ketone (5-1) involves dihydroxylation of the alkene followed by diol cleavage. The glycol (5-2) is first prepared by reacting the alkene (1-4) with osmium tetroxide. This reaction can be carried out either with stochiometric amounts of osmium tetraoxide, or with catalytic amounts of osmium tetraoxide, if an oxidant such as hydrogen peroxide, tert-butyl hydroperoxide, or N-methylmorpholine-N-oxide is present. These reactions can be run in a variety of solvents including: 1,4-dioxane, tetrahydrofuran, tert-butanol and diethyl ether, preferably at 0° to 50 ° C.

The glycol can be cleaved by a variety of reagents including, but not limited to, periodic acid, lead tetraacetate, manganese dioxide, potassium permanganate, sodium metaperiodate, and N-iodosuccinamide. Depending on the cleavage reagent, a variety of solvents can be used. Preferably the cleavage reagent is sodium metaperiodate, the solvent is preferably a mixture of ethanol, methanol or 1,4-dioxane and water and the reaction temperature is 0° C. to 25° C.

Scheme 6

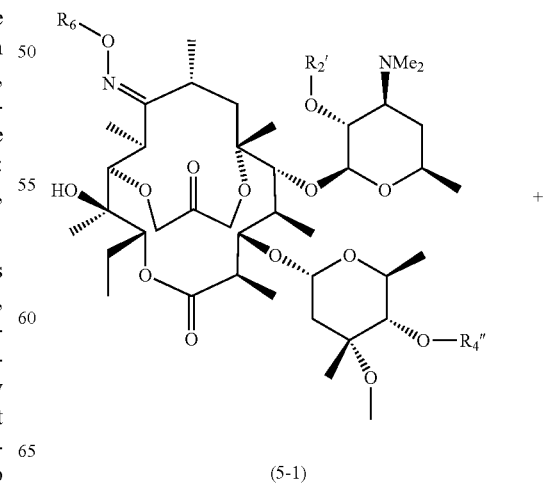

-continued

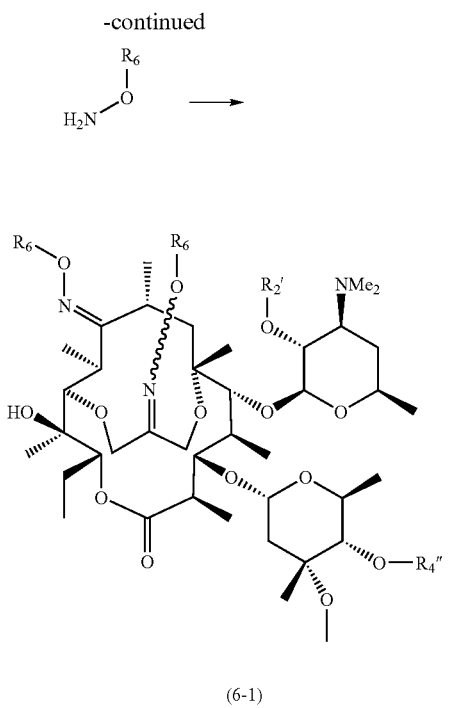

(6-1)

Compounds of formula (5-1) represent useful intermediates which can be further functionalized in a variety of ways. Scheme 6 details a procedure for the conversion of the ketone (5-1) into an oxime of formula (6-1). Oxime formation can be accomplished under either acidic or basic conditions in a variety of solvents. Representative acids include, but are not limited to, hydrochloric, phosphoric, sulfuric, para-toluenesulfonic, and pyridinium p-toluene sulfonate. Likewise bases which are useful are, for example, triethylamine, pyridine, diisopropylethyl amine, 1,5-lutidine, imidazole, and the like. Appropriate solvents include, but are not limited to, methanol, ethanol, water, tetrahydrofuran, 1,2-dimethoxyethane, and ethyl acetate. Preferably the reaction is run in ethanol using triethylamine as the base. The reaction temperature is generally 25° C. to 50° C. and reaction time is 1 to 12 hours.

Scheme 7

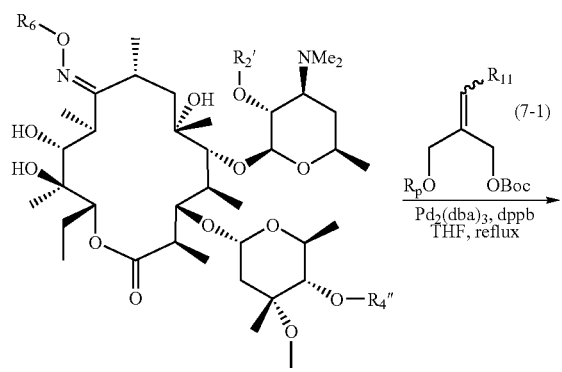

(1-2)

-continued

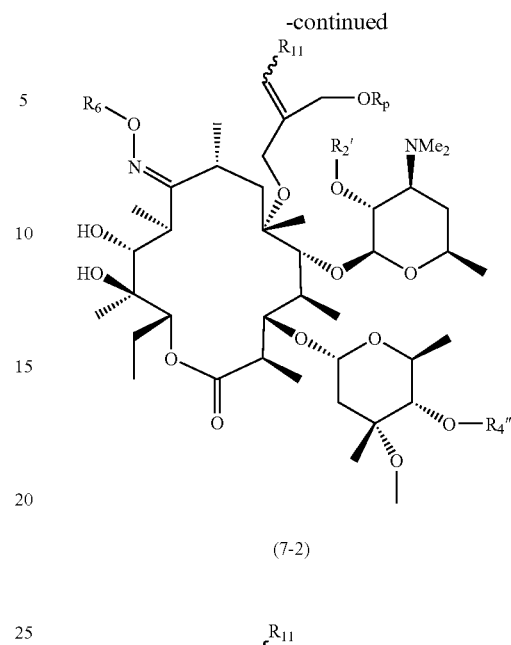

(7-2)

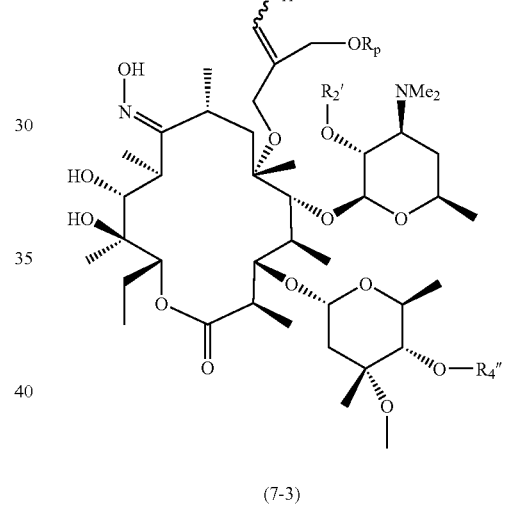

(7-3)

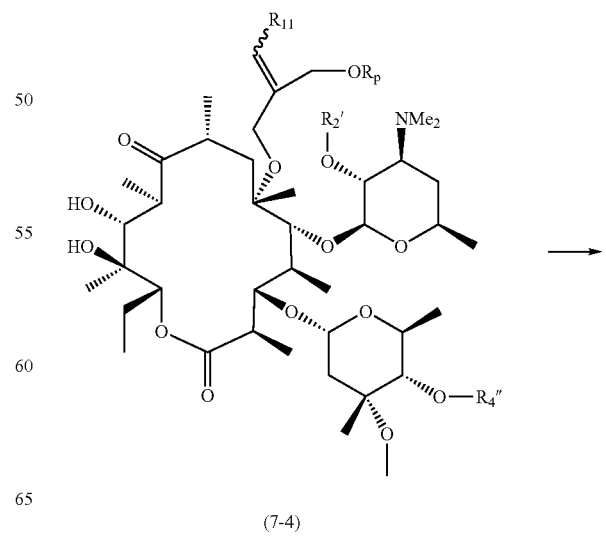

(7-4)

-continued

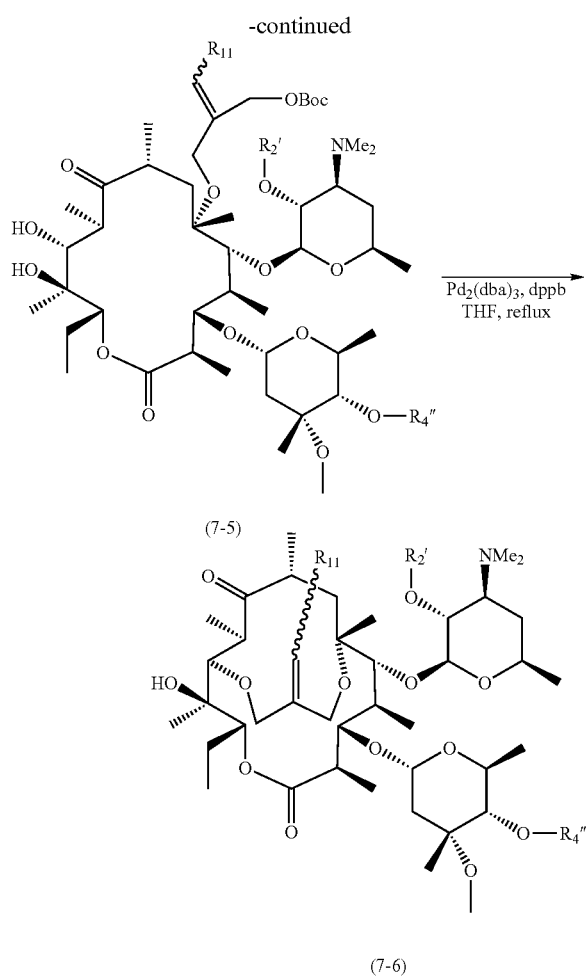

(7-5)

(7-6)

Scheme 7 details a procedure for the stepwise formation of the 6-11 bridged macrolide of formula (7-6). In a similar manner as before, the procedure involves reacting a compound of formula (1-2) with a suitable alkylating agent. As before, the erythromycin derivative of formula (1-2) is reacted with an alkylating agent of the formula:

(7-1)

where $R_{12}$ is $C_1$–$C_{12}$-alkyl and $R_p$ and $R_{11}$ are as previously defined.

Most palladium (0) catalysts are expected to work in this process. Some palladium (II) catalysts, such as palladium (II) acetate, which is converted into a palladium (0) species in-situ by the actions of a phosphine, will work as well. See, for example, Beller et al. *Angew. Chem. Int. Ed. Engl.*, 1995, 34 (17), 1848. The palladium catalyst can be selected from, but not limited to, the group consisting of palladium (II) acetate, tetrakis(triphenylphospine)palladium (0), tris (dibenzylideneacetone)dipalladium, tetradibenzylideneacetone)dipalladium and the like. Palladium on carbon and palladium (II) halide catalysts are less preferred than other palladium catalysts for this process.

Suitable phosphines include, but are not limited to, triphenylphosphine, bis(diphenylphosphino)methane, 1,2-bis(diphenylphosphino)ethane, 1,3-bis(diphenylphosphino)propane, 1,4-bis(diphenylphosphino)butane, 1,5-bis(diphenylphosphino)pentane, and tri(o-tolyl)phosphine, and the like.

The reaction is carried out in an aprotic solvent, preferably at elevated temperature, preferably at or above 50° C.

The aprotic solvents include, but are not limited to, tetrahydrofuran, N,N-dimethylformamide, dimethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. The most preferred solvents are tetrahydrofuran and toluene.

The alkylating agents useful in the process of the invention are the mixed silyl ether carbonates (7-1). Generally, the alkylating agents have the formula (7-1), previously described. The preferred alkylating agents are those wherein $R_{12}$ is tert-butyl, isopropyl or isobutyl and Rp is tert-butyl dimethyl silyl, triisopropyl silyl, tert-butyl diphenyl silyl or the like.

The alkylating reagents of formula (7-1) are prepared by reaction of a diol sequentially with a wide variety of compounds for incorporating the carbonate moiety, followed by a wide variety of compounds for incorporating the silyl moiety. Alkylating reagents include, but are not limited to, tert-butyl chloroformate, di-tert-butyl dicarbonate, and 1-(tert-butoxycarbonyl)imidazole; whereas silylating reagents include, but are not limited to, tert-butyl dimethyl silyl chloride, tert-butyl dimethyl silyl triflate, tert-butyl dimethyl silyl cyanide, and tert-butyl dimethyl silyl imidazole. Both reactions are carried out in the presence of an organic or an inorganic base. The temperature of the reactions varies from about –30° C. to about 30° C. Preferably, the alkylating reagent is di-tert-butyl dicarbonate and the silylating reagent is tert-butyl dimethyl silyl chloride.

The free oxime (7-3) is prepared using essentially the same procedure as for the deprotection of oxime (1-4) where $R_6$ is Ac.

Compounds of formula (7-4) can be formed directly from compounds of formula (7-3) by the application of the previously described procedure for the reduction of oximes of formula (1-4), where $R_6$ is hydrogen, to the corresponding imine of formula (3-1) in Scheme 3.

The protecting group (Rp) is then removed from the hydroxyl of the compound of formula (7-4) using the appropriate conditions as outlined in T. W. Greene and P. G. M. Wuts in "Protective Groups in Organic Synthesis" 3$^{rd}$ ed., John Wiley & Son, Inc, 1999. For example, when the protecting group is TBS, tetra-n-butyl ammonium fluoride, hydrofluoric acid or trifluoroacetic acid may be used. Using standard conditions, the primary hydroxyl is converted to the tert-butyl carbonate, and subsequently the 11-hydroxyl group is alkylated by means of a palladium (0) catalyst as described previously. In this way compounds of formula (7-5) can be prepared readily.

Scheme 8

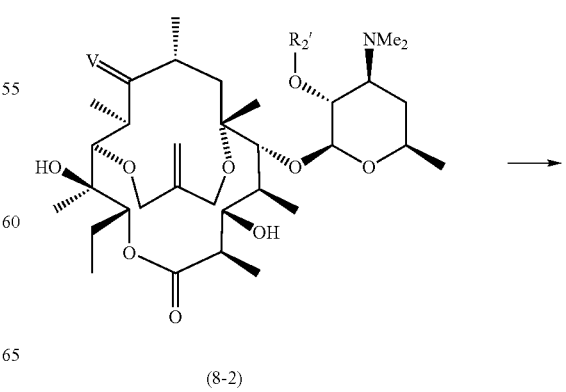

(8-2)

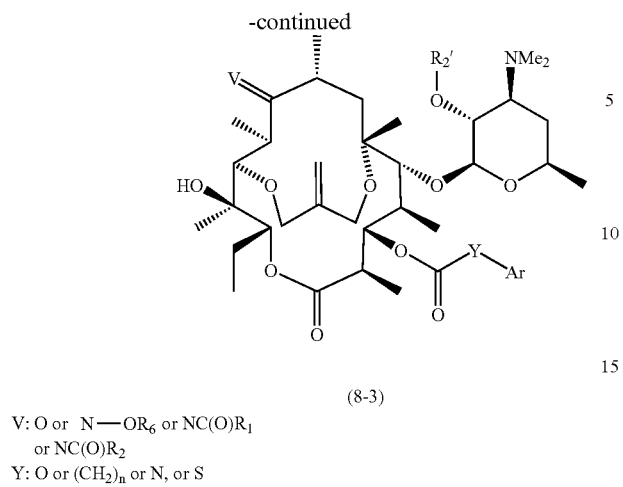

(8-3)

V: O or N—OR$_6$ or NC(O)R$_1$
or NC(O)R$_2$
Y: O or (CH$_2$)$_n$ or N, or S
n: 0–4

Scheme 8 illustrates a procedure for the acylation of the C-3 hydroxyl of compounds of formula (8-2). The hydroxyl group is acylated under basic conditions using a suitable acylating agent in an aprotic solvent. Typical acylating agents include, but are not limited to, acid chlorides, acid anhydrides, and chloroformates.

Typical bases include, but are not limited to, pyridine, triethylamine, diisopropyl ethylamine, N-methyl morpholine, N-methyl pyrolidine, 2,6-lutidine, 1,8-diazabicyclo [5.4.0]undec-7-ene. For a more extensive discourse on acylating conditions see for example, T. W. Greene and P. G. M. Wuts in "Protective Groups in Organic Synthesis" 3$^{rd}$ ed., John Wiley & Son, Inc, 1999.

Scheme 9

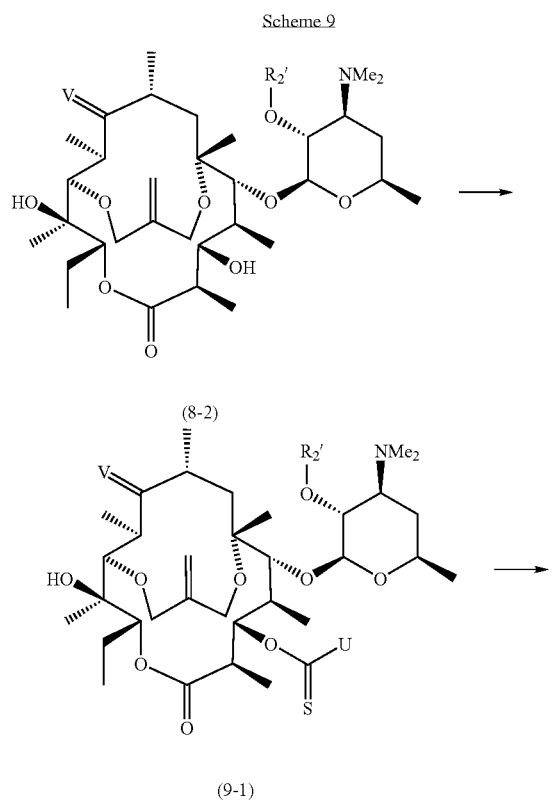

(8-2)

(9-1)

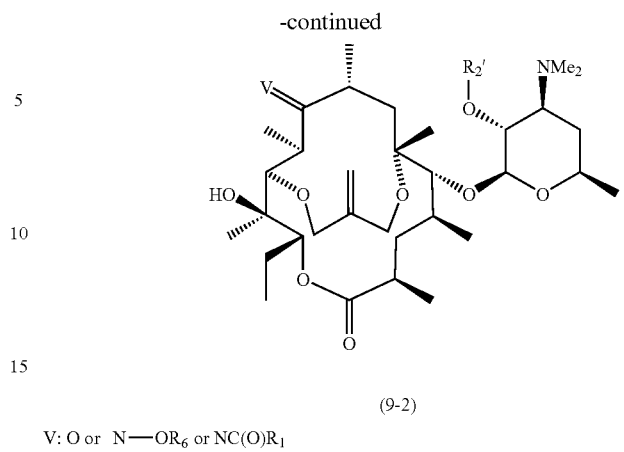

(9-2)

V: O or N—OR$_6$ or NC(O)R$_1$
or NC(O)R$_2$
U: SR or OR

Another process of the invention, as illustrated in Scheme 9, involves the C-3 deoxygenation of the macrolide (8-2) which can be accomplished via the two step procedure shown therein. In the first step the xanthate or thiocarbonate is formed by the reaction of alkoxide of alcohol (8-2) with the appropriate thiocarbonyl. For instance, formation of the xanthate can be accomplished by reaction of the alkoxide with either carbondisulfide followed by methyliodide, or a dithiocarbonyl imidazole; whereas the thiocarbonate can be prepared by the reaction of the alkoxide with either thiocarbonyldimidazole followed by methanol, ethanol or the like, or a thiochloroformate. One skilled in the art will appreciate that other reagents and conditions exist to perform these transformations and that the examples above are for illustrative purposes only and do not limit the scope of this invention. These reactions are typically run in a polar aprotic solvent, preferably THF, acetonitrile, or DMF.

In the second step of Scheme 9, the thiocarbonate or xanthate is decomposed to give the alkane. Most typically this is done under radical conditions using, for example, a silyl hydride such as SiH(TMS)$_3$, SiH$_2$Ph$_2$ or the like, a tin hydride such as Bu$_3$SnH, Ph$_3$SnH or the like, and a radical initiator such as AIBN or t-butyl peroxide. The preferred solvent is toluene.

Scheme 10

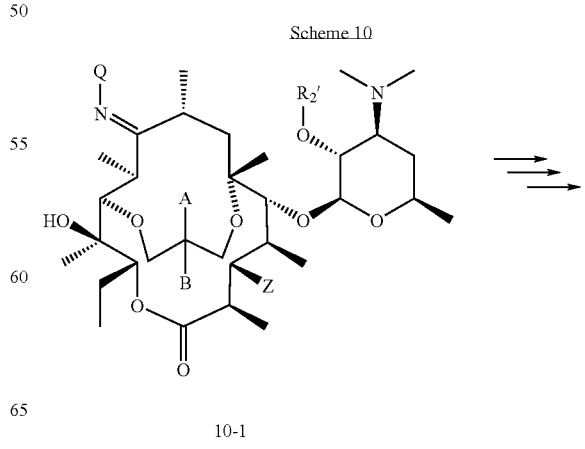

10-1

-continued

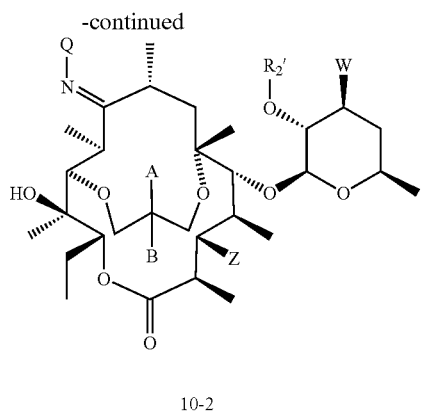

10-2

It will be appreciated that compounds of the present invention include modification of the 3'-N of compounds of the formula (10-1). Compounds of formula (10-2) can be made via the methods delineated in U.S. Pat. Nos. 6,034,069 and 6,387,885.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent tothose skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula IV: A and B Taken Together with the Carbon Atom to Which They are Attached=C=CH$_2$, Q=OH, R$_2$' is H, and R$_4$"=Ac.

Step 1a: Compound of Formula 1-2: R$_6$=Ac, R$_2$'=Ac and R$_4$"=Ac:

Acetic anhydride (35.9 ml, 0.38 mol), triethylamine (55.7 ml, 0.4 mol) and DMAP (3.7 g, 0.03 mol) were added to a solution of the compound of formula (1-2) where R$_6$=R$_2$'=R$_4$"=H (74.9 g, 0.1 mol) in 400 ml of THF at room temperature and the resulting mixture was stirred at room temperature for about 16 hours. The reaction mixture was concentrated to about 200 ml under reduced pressure, diluted with 300 ml of ethyl acetate, washed with saturated NaHCO$_3$ (4×500 ml) and brine (500 ml). The organic phase was dried over sodium sulfate and the solvent was removed in vacuo. The solid residue was recrystallized from ethyl acetate to give the title compound (78 g).

MS (ESI) m/z: 875.46 (M+H)$^+$. $^{13}$C-NMR(100 MHz, CDCl$_3$): δ 178.5, 175.4, 170.6, 170.2, 168.2, 100.2, 96.1, 83.3, 79.3, 78.7, 75.2, 74.5, 72.9, 70.0, 67.6, 63.4, 63.2, 60.6, 49.5, 44.7, 40.9, 35.4, 31.8, 28.5, 22.8, 21.7, 21.6, 21.5, 21.3, 21.2, 21.1, 19.9, 18.6, 18.4, 16.7, 14.9, 14.4, 14.3, 10.8, 9.2

Step 1b: Compound of Formula 1-4: R$_6$=Ac, R$_2$'=Ac and R$_4$"=Ac.

A mixture of the compound from step 1a (21.9 g, 25 mmol), 2-methylene-1,3-propane-[bis-(tert-butyl)carbonate] (18.02 g, 62.25 mmol) and 1,4-bis(diphenylphosphino)-butane (640 mg, 1.5 mmol) was dissolved in freshly distilled THF (250 ml). To the solution was added Pd$_2$(dba)$_3$ (687 mg, 0.75 mmol). The reaction mixture was heated to reflux slowly. After refluxing for 14 hours, the reaction was cooled to room temperaure, diluted with 400 ml ethyl acetate, and washed with saturated NaHCO$_3$ (400 ml) and brine (400 ml). The organic phase was dried over Na$_2$SO$_4$, the solvent was removed in vacuo and the solid residue was purified by silica gel chromatography (acetone:hexane/1:2) to give the title compound (22 g).

MS (ESI) m/z: 927.64 (M+H)$^+$. $^{13}$C-NMR(100 MHz, CDCl$_3$): δ 176.5, 175.9, 170.7, 170.1, 169.9, 141.6, 124.7, 100.4, 96.0, 79.1, 78.7, 78.2, 78.0, 77.4, 76.5, 73.5, 73.0, 72.4, 72.1, 67.8, 66.1, 63.4, 63.3, 49.6, 44.1, 41.2, 40.9, 37.3, 35.4, 35.1, 31.3, 29.5, 28.5, 27.1, 23.4, 21.7, 21.3, 21.1, 20.9, 20.3, 18.8, 18.3, 17.4, 15.7, 13.4, 12.7, 8.6.

Step 1c: Compound of Formula IV: A and B Taken Together with the Carbon Atom to Which They are Attached=C=CH$_2$, Q=OH, R$_2$'=H, and R$_4$"=Ac.

A solution of the compound from step 1b (22 g) in 400 ml methanol was refluxed for 48 hours. The solvent was removed in vacuo and the compound was purified by column chromatography (CH$_2$Cl$_2$: 2M ammonia in MeOH/ 95:5) to give the title compound (18.5 g).

MS (ESI) m/z: 843.67 (M+H)$^+$. $^{13}$C-NMR(100 MHz, CDCl$_3$): δ 176.2, 170.8, 168.8, 142.0, 124.2, 102.5, 95.9, 79.4, 78.7, 78.1, 78.0, 76.6, 73.0, 71.8, 71.1, 68.2, 65.6, 63.2, 49.7, 44.2, 41.7, 40.5, 37.7, 35.0, 34.4, 29.3, 25.8, 23.5, 21.9, 21.3, 21.1, 19.0, 18.1, 17.5, 15.3, 13.2, 12.7, 8.7.

Example 2

Compound of Formula IV: A and B Taken Together with the Carbon Atom to Which are Attached=C=CH$_2$, Q=H, R$_2$'=H, and R$_4$"=Ac.

Formic acid (2.33 ml, 61.7 mmol), water (115 ml) and sodium thiosulfate (9.7 g, 55.5 mol) were added sequentially into a solution of the title compound of example 1 (15.6 g, 18.5 mmol) in isopropanol (10 ml) at room temperature. The reaction mixture was refluxed for 1.5 hour, cooled to room temperature, diluted with ethyl acetate (300 ml), and washed with saturated sodium bicarbonate (2×200 ml) and brine (200 ml). The organic phase was dried over sodium sulfate and the solvent was removed in vacuo. The residue was purified by silica gel chromatography to give the title compound (8.0 g).

MS (ESI) m/z: 827.59 (M+H)$^+$.

$^{13}$C-NMR(100 MHz, CDCl$_3$): δ 190.8, 176.6, 170.7, 142.5, 122.2, 102.4, 96.0, 95.9, 79.9, 78.9, 78.7, 77.9, 76.3, 72.9, 71.1, 68.2, 65.5, 63.2, 50.3, 49.7, 44.5, 41.5, 40.5, 37.5, 35.4, 35.0, 29.1, 23.2, 21.9, 21.4, 21.3, 21.1, 19.8, 18.1, 17.2, 14.6, 13.7, 12.4, 8.8.

Example 3

Compound of Formula V: A and B Taken Together with the Carbon Atom to Which They are Attached=C=CH$_2$, Q=H, and R$_2$'=H.

Method 1

Hydrochloric acid (0.5N, 60 ml) was added to a solution of the compound from Example 2 (5.8 g, 7 mmol) in ethanol (30 ml) at room temperature. The mixture was heated to 65° C. for 2 hours, cooled to room temperature and the pH was adjusted to pH=10 by slow addition of 3N aqueous sodium hydroxide. The aqueous solution was extracted with ethyl acetate (200 ml) and the organic phase was washed once with saturated sodium bicarbonate (200 ml), dried over sodium sulfate and sovent was removed in vacuo. The residue was purified by silica gel chromatography (CH$_2$Cl$_2$: 2M ammonia in methanol/95:5) to give the title compound (2.8 g).

MS (ESI) m/z: 627.56(M+H)$^+$. $^{13}$C-NMR(100 MHz, CDCl$_3$): δ 188.5, 176.0, 143.9, 118.9, 106.9, 90.8, 79.8, 79.6, 79.2, 77.4, 75.9, 75.3, 70.8, 70.4, 65.8, 65.3, 44.6, 42.1, 40.4, 38.6, 36.4, 35.3, 28.2, 22.9, 21.5, 20.0, 19.7, 16.8, 15.1, 14.9, 11.5, 8.3.

Method 2

Titanium trichloride (40 ml, 20% in 3% hydrochloric acid) was added dropwise during 10 minutes into a stirred solution of the compound from step 1c (9.5 g, 11.3 mmol) and ammonia acetate (17.4 g, 226 mmol) in 120 ml of methanol at 0° C. The reaction mixture was allowed to warm up to room temperature and stirred overnight. The pH of the reaction mixture was adjusted to pH=10 by slow addition of 3N aqueous sodium hydroxide. The aqueous solution was extracted with ethyl acetate (200 ml) and the organic phase was washed once with saturated sodium bicarbonate (200 ml), dried over sodium sulfate and solvent was removed in vacuo. The residue was purified by silica gel chromatography (CH$_2$Cl$_2$: 2M ammonia in methanol/95:5) to give the title compound (3.0 g).

MS (ESI) m/z: 627.56 (M+H)$^+$.

Example 4

Compound of Formula V: A and B Taken Together with the Carbon Atom to Which They are Attached=C=CH$_2$, Q=Ac, and R$_2$'=H.

Step 4a: Compound of Formula V: A and B Taken Together with the Carbon Atom to Which They are Attached=C=CH$_2$, Q=Ac, and R$_2$'=Ac.

Acetic anhydride (1.36 ml, 14.4 mmol) was added to a solution of the title compound of Example 3 (3 g, 4.8 mmol) and triethylamine (2.8 ml, 20 mmol) in dichloromethane (40 ml). The reaction mixture was stirred at room temperature for 4 hours, diluted with 100 ml of dichloromethane and washed with saturated sodium bicarbonate (3×100 ml) and brine (100 ml). The organic phase was dried over sodium sulfate and the solvent was removed in vacuo. The residue was purified by silica gel chromatography (hexanes:acetone/1:1) to give title compound (2.9 g).

MS (ESI) m/z: 711.50 (M+H)$^+$. $^{13}$C-NMR(100 MHz, CDCl$_3$): δ 184.7, 176.9, 174.9, 170.1, 141.9, 122.2, 99.4, 81.2, 79.0, 77.8, 77.7, 76.1, 73.5, 71.7, 68.8, 65.7, 63.2, 43.7, 40.8, 39.9, 38.2, 36.2, 35.6, 31.0, 25.5, 23.2, 21.6, 21.2, 19.9, 19.5, 17.1, 15.8, 14.7, 11.8, 7.9.

Step 4b: Step 4a: Compound of Formula V: A and B Taken Together with the Carbon Atom to Which They are Attached=C=CH$_2$, Q=Ac, and R$_2$'=H.

The title compound is prepared by refluxing the compound from step 4a in methanol according to the procedure described in Example 1 (Step 1c).

Example 5

Compound of Formula IV: A and B Taken Together with the Carbon Atom to Which They are Attached=C=CH$_2$, Q=O—CH$_2$OCH$_3$, R$_2$'=H, and R$_4$''=Ac.

Step 5a: Compound of Formula IV: A and B Taken Together with the Carbon Atom to Which They are Attached=C=CH$_2$, Q=OH, R$_2$'=Ac, and R$_4$''=Ac.

1M LiOH (10 ml) was added to a solution of the compound from step 1b (1.85 g, 2 mmol) in 10 ml THF and 10 ml isopropanol at room temperature. After stirring at room temperature for 30 minutes, the reaction mixture was diluted with saturated sodium bicarbonate (40 ml) and extracted with ethyl acetate (2×40 ml). The organic phase was washed with brine (2×40 ml), dried over sodium sulfate and the solvent was removed in vacuo. The residue was purified by silica gel chromatography (hexanes:acetone, 1:1) to give the title compound (1.65 g).

MS (ESI) m/z: 885.45 (M+H)$^+$. $^{13}$C-NMR(100 MHz, CDCl$_3$): δ 175.9, 170.7, 170.1, 168.7, 142.0, 142.2, 100.5, 95.9, 79.4, 78.6, 78.1, 77.9, 76.6, 73.0, 72.8, 72.0, 71.7, 67.7, 65.5, 63.5, 63.2, 49.6, 44.1, 41.4, 40.9, 37.4, 35.0, 34.4, 31.7, 31.3, 25.7, 23.5, 21.7, 21.3, 19.0, 18.1, 17.5, 15.3, 13.2, 12.7, 8.6

Step 5b: Compound of Formula IV: A and B Taken Together with the Carbon Atom to Which They are Attached=C=CH$_2$, Q=O—CH$_2$OCH$_3$, R$_2$'=Ac, and R$_4$''=Ac.

Sodium hydride (33 mg, 1.3 mmol) was added into a solution of the title compound of example 5a (885 mg, 1 mmol) in 10 ml DMF at 0° C. MOM-Cl (90 μl, 1.2 mmol) was added and stirred at 0° C. overnight. The reaction mixture was diluted with ethyl acetate (20 ml) and quenched with saturated NaHCO$_3$, washed with brine (20 ml) and dried over anhydrous sodium sulfate. The residue was purified by silica gel chromatography to give the title compound (0.4 g).

MS (ESI) m/z: 929.49 (M+H)$^+$. $^{13}$C-NMR(100 MHz, CDCl$_3$): δ 175.9, 170.7, 170.1, 169.5, 142.1, 124.5, 100.5, 98.4, 96.0, 79.3, 78.7, 78.2, 78.1, 77.2, 76.5, 72.9, 72.0, 71.8, 67.7, 65.9, 63.4, 63.2, 56.6, 49.6, 44.1, 41.4, 40.9, 37.2, 35.0, 34.8, 34.6, 31.3, 28.0, 27.0, 25.4, 23.4, 21.7, 21.3, 21.1, 20.8, 19.0, 18.2, 17.4, 15.5, 13.3, 12.7, 8.6.

Step 5c. Compound of Formula IV: A and B Taken Together with the Carbon Atom to Which They are Attached=C=CH$_2$, Q=O—CH$_2$OCH$_3$, R$_2$'=H, and R$_4$''=Ac.

The title compound was prepared by refluxing the compound from Step 5b in methanol according to the procedure described in Example 1 (Step 1c).

MS (ESI) m/z: 887 (M+H)$^+$.

Example 6

Compound of Formula V: A and B Taken Together with the Carbon Atom to Which They are Attached=C=CH$_2$, Q=O—CH$_2$OCH$_3$, and R$_2$'=H.

Step 6a: Compound of Formula V: A and B Taken Together with the Carbon Atom to Which They are Attached=C=CH$_2$, Q=OH, and R$_2$'=Ac.

To a solution of the title comound of example 1 (4.2 g, 4.5 mmol) in 50 ml methanol was added 2M HCl (10 ml). The reaction mixture was refluxed for 1.5 hours and then condensed to 30 ml. Saturated sodium bicarbonate (30 ml) was added and the mixture was extracted with ethyl acetate (50 ml). The organic phase was dried over sodium sulfate and solvent was removed in vacuo. The residue was purified by silica gel chromatography (hexane:acetone/1:1) to give the title compound (2.5 g).

MS (ESI) m/z: 685.45 (M+H)$^+$. $^{13}$C-NMR(100 MHz, CDCl$_3$): δ 175.2, 170.2, 166.3, 143.6, 119.3, 99.6, 82.2, 79.5, 78.1, 77.5, 76.0, 73.7, 71.7, 68.9, 65.5, 63.3, 43.8, 40.8, 37.4, 35.9, 34.3, 31.1, 25.6, 23.3, 21.7, 21.3, 19.9, 19.6, 17.1, 15.7, 14.7, 11.9, 7.9

Step 6b: Compound of Formula I: A and B Taken Together with the Carbon Atom to Which They are Attached=C=CH$_2$, Q=O—CH$_2$CH$_3$, and R$_2$'=Ac.

To a solution of the compound from step 6a (6.85 g, 10 mmol) in 40 ml DMF was added NaH (303 mg, 1.3 mmol) at 0° C. portion wise. After 10 minutes, MOM-Cl (900 μl, 1.15 mmol) was added at 0° C. during 15 minutes. The reaction mixture was stirred at 0° C. for 16 hours, diluted with ethyl acetate (100 ml) and quenched with saturated sodium bicarbonate (60 ml). The organic layer was separated, washed with brine (60 ml) and dried over sodium sulfate. The solvent was removed on vacuo and the residue was purified by silica gel chromatography (hexane:acetone/1:1) to give the title compound (4.5 g).

MS (ESI) m/z: 729 (M+H)$^+$.

Step 6c. Compound of Formula I: A and B Taken Together with the Carbon Atom to Which They are Attached=C=CH$_2$, Q=O—CH$_2$OCH$_3$, and R$_2$'=H.

The title compound of Example 6 was prepared by refluxing the compound from Step 6b in methanol according to the procedure described in Example 1 (Step 1c).

MS (ESI) m/z: 687 (M+H)$^+$.

Example 7

Compound of Formula I: A and B Taken Together with the Carbon Atom to Which They are Attached=C=CH$_2$, X and Y Taken Together with the Carbon Atom to Which They are Attached=C=NAc, L=CH$_2$CH$_3$, W is N(CH$_3$)$_2$, Z=H and R$_2$'=H Step 7a: Compound of Formula I: A and B Taken Together with the Carbon Atom to Which They are Attached=C=CH$_2$, X and Y Taken Together with the Carbon Atom to Which They are Attached=C=NAc, L=CH$_2$CH$_3$, W is N(CH$_3$)$_2$, Z=H and R$_2$'=Ac.

The title compound is prepared from the compound of Step 4a, sodium hydride, carbon disulfide and tri-n-butyl tin hydride according to the procedures described in the literature. For further details, see Elliott, Richard L.; Pireh, Daisy; Griesgraber, George; Nilius, Angela M.; Ewing, Patty J.; Bui, Mai Ha; Raney, Patti M.; Flamm, Robert K.; Kim, Ki; Henry, Rodger F.; Chu, Daniel T. W.; Plattner, Jacob J.; Or, Yat Sun. J. Med. Chem. (1998), 41(10), 1651–1659.

Step 7b: Compound of Formula I: A and B Taken Together with the Carbon Atom to Which They are Attached=C=CH$_2$, X and Y Taken Together with the Carbon Atom to Which They are Attached=C=NAc, L=CH$_2$CH$_3$, W is N(CH$_3$)$_2$, Z=H and R$_2$'=H.

The title compound is prepared by refluxing the compound from step 7a in methanol according to the procedure described in Example 1 (Step 1c).

Example 8

Compound of Formula I: A and B Taken Together with the Carbon Atom to Which They are Attached=C=CH$_2$, X and Y Taken Together with the Carbon Atom to Which They are Attached=C=NAc, L=CH$_2$CH$_3$, Z=OC(O)(p-nitrophenyl) and R$_2$'=H Step 8a: Compound of Formula I: A and B Taken Together with the Carbon Atom to Which They are Attached=C=CH$_2$, X and Y Taken Together with the Carbon Atom to Which They are Attached=C=NAc, L=CH$_2$CH$_3$, W is N(CH$_3$)$_2$, Z=OC(O)(p-nitrophenyl) and R$_2$'=Ac.

The title compound is prepared from the compound of Step 4a of Example 4, sodium hydride, and para-nitrobenzoyl fluoride according to the procedures described in the literature. For further details, see Misawa et al, 6-O-Desosaminylerythronolide derivatives, U.S. Pat. No. 5,602,239.

Step 8b. Compound of Formula I: A and B Taken Together with the Carbon Atom to Which They are Attached=C=CH$_2$, X and Y Taken Together with the Carbon Atom to Which They are Attached=C=NAc, L=CH$_2$CH$_3$, W is N(CH$_3$)$_2$ Z=OC(O)(p-nitrophenyl) and R$_2$'=H.

The title compound is prepared by refluxing the compound from step 8a in methanol according to the procedure described in Example 1 (Step 1c).

Example 9

Compound of Formula I: A and B Taken Together with the Carbon Atom to Which They are Attached=C=CH$_2$, X and Y Taken Together with the Carbon Atom to Which They are Attached=C=NAc, L=CH$_2$CH$_3$, W is N(CH$_3$)$_2$, Z=OC(O)[2-(NO$_2$), 4-(CF$_3$)Phenyl] and R$_2$'=H.

The title compound is prepared from the compound of Step 4a of Example 4, 2-nitro-4-trifluoromethylbenzoyl fluoride and sodium hydride followed by reaction in methanol according to the procedures described in Example 8.

Example 10

Compound of Formula I: A and B Taken Together with the Carbon Atom to Which They are Attached=C=CH$_2$, X and Y Taken Together with the Carbon Atom to Which They are Attached=C=NAc, L=CH$_2$CH$_3$, W is N(CH$_3$)$_2$, Z=OC(O)CH$_2$(p-methoxyphenyl) and R$_2$'=H.

Step 10a: Compound of Formula I: A and B Taken Together with the Carbon Atom to Which They are Attached=C=CH$_2$, X and Y Taken Together with the Carbon Atom to Which They are Attached=C=NAc, L=CH$_2$CH$_3$, W is N(CH$_3$)$_2$, Z=OC(O)CH$_2$(p-methoxyphenyl) and R$_2$'=Ac.

The title compound is prepared from the compound of Step 4a of Example 4, p-methoxyphenyl acetic acid, pivaloyl chloride, and triethylamine in a solution of pyridine and dichloromethane according to the procedure described in the literature. For further details, see Morimoto et al, 5-O-Desosaminylerythronolide derivatives, EP 0619320, and WO 99/21868.

Step 10b: Compound of Formula I: A and B Taken Together with the Carbon Atom to Which They Attached=C=CH$_2$, X and Y Taken Together Together with the Carbon Atom to Which They are Attached=C=NAc, L=CH$_2$CH$_3$, W is N(CH$_3$)$_2$, Z=OC(O)CH$_2$(p-methoxyphenyl) and R$_2$'=H.

The title compound is prepared by refluxing the compound from Step 10a in methanol according to the procedure described in Example 1 (Step 1c).

Example 11

Compound of Formula IV: A and B Taken Together with the Carbon Atom to Which They are Attached=C=CH$_2$, Q=Ac, R$_2$'=H, and R$_4$"=Ac.

Step 11a. Compound of Formula IV: A and B Taken Together with the Carbon Atom to Which They are Attached=C=CH$_2$, Q=Ac, R$_2$=Ac, and R$_4$"=Ac.

The title compound was prepared from the title compound of Example 6, acetic anhydride, triethylamine and dimethylaminopyridine according to the procedures described in Example 4 (Step 4a).

MS (ESI) m/z: 911 (M+H)$^+$.

Step 11b. Compound of Formula IV: A and B Taken Together with the Carbon Atom to Which They are Attached=C=CH$_2$, Q=Ac, R$_2$'=H, and R$_4$"=Ac.

The title compound of Example 11 is prepared by refluxing the compound from Step 11a in methanol according to the procedure described in Example 1 (Step 1c).

Example 12

Compound of Formula I: Compound of Formula IV: A and B Taken Together with the Carbon Atom to Which They are Attached=C=O, Q=Ac, R$_2$'=H, and R$_4$"=Ac.

Ozone is bubbled into a solution of the title compound of Example 11 in methanol and dichloromethane at −78° C. until the solution turns light blue. Excess ozone is removed by bubbling with nitrogen. Triphenylphosphine is added and the solution is allowed to warm up to room temperature. The solvent is removed in vacuo and the solid residue is re-dissolved in tetrahydrofuran. The resulting solution is refluxed overnight. The title compound of Example 12 is purified by silica gel chromatography.

Example 13

Compound of Formula IV: A and B Taken Together with the Carbon Atom to Which They are Attached=C=OBz, Q=Ac, R$_2$'=H, and R$_4$"=Ac.

O-benzyl hydroxylamine and the title compound of Example 12 are dissolved in ethanol. The reaction mixture is stirred at room temperature for 1 hour. The solvent is removed and the title compound is purified by silica gel chromatography.

Example 14

Compound of Formula IV: A and B Taken Together with the Carbon Atom to Which They are Attached=C=(3-quinolyl), Q=Ac, R$_2$'=H, and R$_4$"=Ac.

The title compound is prepared from the title compound of Example 13, 18, 3-bromoquinoline, and palladium (II) catalyst according to the procedures described in the literature. For further details, see Or, Yat Sun; Clark, Richard F.; Wang, Sanyi; Chu, Daniel T. W.; Nilius, Angela M.; Flamm, Robert K.; Mitten, Michael; Ewing, Patty; Alder, Jeff; Ma, Zhenkun. *J. Med. Chem.* (2000), 43(6), 1045–1049.

Example 15

Compound of Formula I: A and B Taken Together with the Carbon Atom to Which They are Attached=C=CH$_2$, X and Y Taken Together with the Carbon Atom to Which They are Attached=C=O, L=CH$_2$CH$_3$, W is N(CH$_3$)$_2$, Z=4-acetoxy-cladinose and R$_2$'=H Step 15a: Compound of Formula 7-2: R$_6$=Ac, R$_{11}$=H, R$_p$=tert-butyldimethylsilyl, R$_2$'=Ac, and R$_4$"=Ac.

tert-Butyl-OC(O)—OCH$_2$(C=CH$_2$)CH$_2$-O-tert-butyldimethylsilyl (0.9 g, 3 mmol) and 1,4-bis(diphenylphosphino)butane (170 mg, 0.4 mmol) and Pd$_2$(dba)$_3$ (183 mg, 0.2 mmol) were added into a solution of the compound of formula (1-2), R$_6$=R$_2$'=R$_4$"=Ac (1.75 g, 2 mmol) in tetrahydrofuran (10 ml) at room temperature. The reaction mixture was refluxed under nitrogen overnight, cooled to room temperature and the solvent was removed in vacuo. The residue was purified by silica gel chromatography (acetone:hexane/1:3) to give the title compound (1.5 g).

MS (ESI) m/z: 1059.65 (M+H)$^+$. $^{13}$C-NMR(100 MHz, CDCl$_3$): δ 181.2, 179.3, 175.9, 175.5, 173.5, 148.5, 116.5, 104.8, 102.0, 85.2, 84.3, 83.9, 83.6, 82.8, 82.2,79.7, 78.1, 77.6, 75.6, 72.4, 70.4, 69.0, 68.6, 54.6, 49.9, 46.2, 43.2, 40.8, 36.5, 33.6, 31.4, 27.1, 27.0, 26.6, 26.3, 25.2, 25.1, 24.0, 23.7, 22.0, 20.4, 16.0, 15.2, 0.5, 0.0

Step 15b: Compound of Formula 7-2: R$_6$=H, R$_{11}$=H, R$_p$=tert-butyldimethylsilyl, R$_2$'=H, and R$_4$"=Ac.

A solution of the compound from Step 15a (3.18 g, 3 mmol) in methanol (80 ml) was refluxed for 8 hours. The reaction was cooled to room temperature, the solvent was removed in vcauo and the residue was purified by silica gel chromatography (2M ammonia in methanol:dichloromethane/3:97) to give the title compound (2.6 g).

MS (ESI) m/z: 975.47 (M+H)$^+$. $^{13}$C-NMR(100 MHz, CDCl$_3$): δ 179.5, 178.9, 175.7, 150.6, 121.5, 106.8, 101.4, 85.3, 83.9, 83.7, 82.4, 82.0, 79.3, 77.8, 76.7, 76.5, 72.7, 70.4, 70.1, 69.3, 68.3, 54.6, 49.8, 45.5, 43.0, 42.9, 40.6, 38.1, 34.0, 31.1, 30.5, 27.1, 26.3, 26.1, 26.0, 24.3, 23.7, 23.5, 21.5, 19.9, 15.7, 14.8, 0.5, 0.0.

Step 15c: Compound of Formula 7-4: R$_{11}$=H, R$_p$=H, R$_2$'=H, and R$_4$"=Ac.

Formic acid (0.38 ml, 10 mmol) and Na$_2$S$_2$O$_4$ (1.39, 8 mmol) was added into an emulsion of the compound from Step 15b (2.44 g, 2.5 mmol) in isopropanol (25 ml) and water (30 ml). The mixture was heated to 90° C. and stirred at that temperature for 8 hours. The reaction mixture was cooled to room temperature, diluted with ethyl acetate (60 ml), washed with saturated sodium bicarbonate (3×60 ml), and dried over sodium sulfate. The solvent was removed in vacuo and the residue was purified by silica gel chromatography (2M ammonia in methanol:dichloromethane/3:97) to give the title compound (1.7 g).

MS (ESI) m/z: 846.54 (M+H)$^+$. $^{13}$C-NMR(100 MHz, CDCl$_3$): δ 221.3, 175.3, 170.6, 147.0, 114.1, 101.8, 96.6, 79.9, 79.2, 78.8, 78.7, 77.4, 75.0, 72.8, 71.4, 68.8, 67.8, 65.4, 65.3, 63.7, 63.4, 60.6, 49.6, 45.5, 44.8, 40.4, 38.2, 38.0, 35.6, 22.0, 21.2, 21.1, 19.6, 18.6, 16.5, 14.4, 12.2, 10.6, 9.8.

Step 15d: Compound of Formula 7-4: R$_{11}$=H, R$_p$=H, R$_2$=Ac, and R$_4$"=Ac.

Acetic anhydride (94 μl, 1 mmol) was added to a solution of the compound from Step 15c (338.4 mg, 0.4 mmol) in dichloromethane (5 ml). The mixture was stirred at room temperature for 16 hours. The solvent was removed in vacuo and the residue was purified by silica gel chromatography (acetone:hexane/4:6) to give the title compound (330 mg).

MS (ESI) m/z: 888.58 (M+H)$^+$. $^{13}$C-NMR(100 MHz, CDCl$_3$): δ 221.3, 175.1, 170.6, 170.3, 146.8, 114.2, 99.6, 96.5, 79.9, 79.1, 78.5, 78.4, 77.1, 74.9, 72.8, 72.1, 68.9, 67.1, 65.1, 63.7, 63.5, 63.1, 49.3, 45.5, 44.8, 40.6, 38.0, 37.7, 37.6, 35.5, 29.4, 21.8, 21.3, 21.1, 21.0, 19.4, 18.6, 16.6, 12.2, 10.6, 9.6.

Step 15e: Compound of Formula 7-4: $R_{11}$=H, $R_p$=tert-butoxycarbonyl, $R_2'$=Ac, and $R_4$=Ac.

Di-tert-butyl-dicarbonate (69 µl, 0.3 mmol) was added to a solution of the compound of Step 15d (178 mg, 0.2 mmol) and triethylamine (56 µl, 0.4 mmol) in dichloromethane (8 ml) at room temperature. After 10 minutes, N,N-dimethylamino pyridine (12.2 mg, 0.1 mmol) was added. The resulting solution was stirred at room temperature for 2 hours. The solvent was removed in vacuo and the residue was purified by silica gel chromatography (acetone:hexane/1:3) to give the title compound (180 mg).

MS (ESI) m/z: 988.41 (M+H)$^+$. $^{13}$C-NMR(100 MHz, CDCl$_3$): δ 219.6, 174.6, 170.6, 170.3, 153.8, 141.3, 116.8, 99.6, 96.5, 82.0, 80.2, 79.4, 78.7, 78.6, 76.8, 74.9, 72.9, 72.4, 69.1, 67.9, 67.2, 64.8, 63.6, 63.4, 49.4, 45.2, 44.8, 41.0, 37.9, 37.7, 37.6, 35.6, 31.8, 31.3, 31.2, 28.2, 28.1, 22.9, 21.8, 21.5, 21.4, 21.1, 19.4, 18.7, 16.7, 16.6, 14.4, 12.5, 10.7, 9.7.

Step 15f: Compound of Formula I: A and B Taken Together with the Carbon Atom to Which They are Attached=C=CH$_2$, X and Y Taken Together with the Carbon Atom to Which They are Attached=C=O, L=CH$_2$CH$_3$, W is N(CH$_3$)$_2$, Z=4-acetoxycladinose and $R_2'$=Ac.

1,4-bis(diphenylphosphino)butane (8.5 mg, 0.02 mmol) and Pd$_2$(dba)$_3$ (9.2 mg, 0.01 mmol) were added to a solution of the compound of Step 15e (98.8 mg, 0.1 mmol) in 2 ml anhydrous THF at room temperature. The resulting mixture was refluxed for 30 minutes. The solvent was removed in vacuo and the residue was used for next step reaction without purification.

MS (ESI) m/z: 870.49 (M+H)$^+$.

Step 15g. Compound of Formula I: A and B Taken Together with the Carbon Atom to Which They are Attached=C=CH$_2$, X and Y Taken Together with the Carbon Atom to Which They are Attached=C=O, L=CH$_2$CH$_3$, W is N(CH$_3$)$_2$, Z=4-acetoxycladinose and $R_2'$=H.

A solution of the compound of Step 15f (87 mg, 0.01 mmol) in 5 ml methanol was refluxed for 8 hours. The solvent was removed in vacuo and the residue was purified by silica gel chromatography (CH$_2$Cl$_2$: 2M ammonia in CH$_3$OH/97:3) to give the title compound (70 mg).

MS (ESI) m/z: 828.50 (M+H)$^+$. $^{13}$C-NMR(100 MHz, CDCl$_3$): δ 219.1, 17601, 170.8, 14103, 125.7, 102.7, 96.0, 79.2, 78.8, 77.9, 77.2, 76.9. 73.0, 72.3, 71.1, 70.2, 68.4, 65.8, 65.6, 63.3, 49.9, 46.6, 44.5, 41.9, 40.6, 39.4, 38.9, 35.2, 29.1, 23.3, 21.9, 21.4, 21.2, 20.7, 18.3, 17.9, 13.5, 12.6, 8.7.

Example 16

Compound of Formula I: A and B Taken Together with the Carbon Atom to Which They are Attached=C=CH-quinolin-3-yl, X and Y Taken Together with the Carbon Atom to Which They are Attached=C=O, L=CH$_2$CH$_3$, W is N(CH$_3$)$_2$, Z=4-acetoxycladinose and $R_2'$=H.

To a solution of the title compound from Example 15 (992 mg, 1.2 mmol), 3-bromoquinoline (340 µl, 2.5 mmol) and triethyl amine (836 µl, 6 mmol) in acetoitrile (12 ml) was added P(o-Tol)$_3$ (146 mg, 0.48 mmol) and palladium acetate (54 mg, 0.24 mmol) at room temperature. The mixture was degassed and heated to 80° C. and stirred for 16 hours. The mixture was diluted with ethyl acetate (50 ml) and washed with NaHCO$_3$ (60 ml×2) and brine (60 ml). The solvent was removed in vacuo and the residue was purified by silica gel chromatography (CH$_2$Cl$_2$: 2M ammonia in CH$_3$OH/97:3) to give the title compound.

MS (ESI) m/z: 955 (M+H)$^+$.

Example 17

Compound of Formula I: A and B Taken Together with the Carbon Atom to Which They are Attached=C=CH-quinolin-3-yl, X and Y Taken Together with the Carbon Atom to Which They are Attached=C=O, L=CH$_2$CH$_3$, W is N(CH$_3$)$_2$, Z=OH, and $R_2'$=H.

To a solution of the title compound from Example 16 (150 mg, 0.16 mmol) in ethanol(3 ml) was added 5 ml of 5N HCl. The mixture was heated to 65° C. and stirred for 2 hours. The reaction was quenched with saturated NaHCO$_3$ (25 ml) and extracted with ethyl acetate (25 ml). The extract was washed with brine and dried ove anhydrous Na$_2$SO$_4$. The solvent was removed in vacuo and the residue was purified by silica gel chromatography (CH$_2$Cl$_2$: 2M ammonia in CH$_3$OH/97:3) to give the title compound.

MS (ESI) m/z: 755 (M+H)$^+$.

Example 18

Compound of Formula I: A and B Taken Together with the Carbon Atom to Which They are Attached=C=CH$_2$, X and Y Taken Together with the Carbon Atom to Which They are Attached=C=O, L=CH$_2$CH$_3$, W is N(CH$_3$)$_2$, Z=OH and $R_2'$=H.

Step 18a: Compound of Formula I: A and B Taken Together with the Carbon Atom to Which They are Attached=C=CH$_2$, X and Y Taken Together with the Carbon Atom to Which They are Attached=C=O, L=CH$_2$CH$_3$, W is N(CH$_3$)$_2$, Z=OH and $R_2'$=Ac.

To a solution of the compound of Step 15f of Example 15 (700 mg, 0.8 mmol) in 10 ml of ethanol was added 25 ml of 1M HCl. The mixture was refluxed for 2 hours and then cooled to room temperature. The pH of the mixture was adjusted to pH=10 by addition of 2M NaOH and the mixture was extracted with ethyl acetate (25 ml×3). The organic phases were dried over Na$_2$SO$_4$ and the solvent was removed in vacuo. The residue was purified by silica gel chromatography (hexanes:aceton/1:1) to give the title compound (480 mg).

MS (ESI) m/z: 670.23 (M+H)$^+$. $^{13}$C-NMR(100 MHz, CDCl$_3$): δ 216.3, 175.0, 170.1, 141.8, 122.1, 99.4, 81.1, 79.0, 77.7, 77.5, 76.2, 75.6, 72.1, 71.7, 68.8, 65.6, 63.2, 60.5, 46.5, 43.7, 40.8, 39.1, 38.6, 35.9, 31.1, 23.0, 21.6, 21.3, 21.2, 19.8, 18.5, 17.3, 14.8, 14.3, 13.0, 11.7, 7.9.

Step 81b. Compound of Formula I: A and B Taken Together with the Carbon Atom to Which They are Attached=C=CH$_2$, X and Y Taken Together with the Carbon Atom to Which They are Attached=C=O, L=CH$_2$CH$_3$, W is N(CH$_3$)$_2$, Z=OH and $R_2'$=H.

The title compound is prepared by refluxing the compound from Step 18a in methanol according to the procedure described in Example 1 (Step 1c).

Example 19

Compound of Formula IV: A and B Taken Together with the Carbon Atom to Which They are Attached=C=CH$_2$-phenyl, Q=OH, R$_2$'=H, and R$_4$"=Ac.

Step 19a: t-BuOC(O)OCH$_2$C(O)CH$_2$OC(O)OtBu

To a solution of 1,3-dihydroxyacetone dimer (36.03 g, 0.20 mol) and DMAP (1.22 g, 10.0 mmol) in dichloromethane (80 mL) and pyridine (97.0 mL, 1.20 mol) was added a solution of di-tert-butyl dicarbonate (200.0 g, 0.92 mol) in dichloromethane (40 mL) via a dropping funnel over 3 hours at room temperature. After stirring at room temperature for 15 hours, the reaction mixture was condensed in vacuo. The residue was diluted with hexane:diethyl ether/1:1 and washed with saturated aqueous CuSO$_4$, water and brine. The organic phase was dried over Na$_2$SO$_4$ and the solvent was removed in vacuo. The residue was purified by silica gel chromatography (hexane:ethyl acetate/95:5~85:15) to give the title compound (45.0 g, 39% yield).

$^{13}$C-NMR (125 MHz, CDCl$_3$): δ 198.5, 152.6, 83.5, 68.5, 27.6.

Step 19b: Compound of Formula 1-3 of Scheme 1: R=Phenyl and R$_{11}$=t-Butyl.

A suspension of benzyltriphenylphosphonium bromide (520 mg, 1.20 mmol) in THF (5.0 mL) was treated with n-butyl lithium (1.6 M in hexane, 0.81 mL, 1.30 mmol) at −78° C. under nitrogen with stirring. The mixture was warmed to −15° C. over 1 hour before a solution of the compound from Step 19a (290 mg, 1.0 mmol) in THF (2.5 mL) was charged at −70° C. The reaction mixture was warmed to room temperature over 1 hour and left stirring for another 14 hours before partition (ethyl acetate and water). The organic phase was washed with water, brine and dried over Na$_2$SO$_4$. The solvent was evaporated and the residue was purified by silica gel chromatography (hexane:CH$_2$Cl$_2$/1:1) to give the title compound (253 mg, 70% yield).

$^{13}$C-NMR (125 MHz, CDCl$_3$): δ 153.1, 153.0, 135.1, 134.6, 130.4, 128.6, 128.2, 127.6, 82.0, 81.9, 68.4, 62.7, 27.6, 27.5.

Step 19c: Compound of Formula IV: A and B Taken Together with the Carbon Atom to Which They are Attached=C=CH$_2$-phenyl, Q=OAc, R$_2$'=Ac, and R$_4$"=Ac.

A mixture of Erythromycin A oxime triacetate (525 mg, 0.60 mmol), the compound from Step 19b (250 mg, 0.69 mmol), 1,4-bis(diphenylphosphino)butane (51.2 mg, 0.12 mmol), and tris(dibenzylideneacetone)dipalladium (54.9 mg, 0.06 mmol) in THF (5.0 mL) was degassed and heated to and kept at 75° C. for 15 hours before evaporation. The residue was purified by silica gel chromatography (hexane:acetone/4:1~1.5:1) to give the title compound as a 2.6:1 isomeric mixture (330 mg, 55% yield).

MS (ESI) m/z: 1003 (M+H)$^+$.

Step 19d: Compound of Formula IV: A and B Taken Together with the Carbon Atom to Which They are Attached=C=CH$_2$-phenyl, Q=OH, R$_2$'=H, and R$_4$"=Ac.

The title compound was prepared by refluxing the compound from Step 19c in methanol according to the procedure described in Example 1 (Step 1c).

MS (ESI) m/z: 919 (M+H)$^+$.

Example 20

Compound of Formula V: A and B Taken Together with the Carbon Atom to Which They are Attached are C=CH-phenyl, Q=Ac, and R$_2$'=H.

Step 20a: Compound of Formula V: A and B Taken Together with the Carbon Atom to Which They are Attached are C=CH-phenyl, Q=H, and R$_2$'=Ac.

A solution of the compound of Example 19 (0.30 mmol) in methanol (5.0 mL) was treated with titanium(III) chloride (20% in 3% HCl, 0.77 mL) for 2 hours at room temperature then for 1 hour at 50° C. before partition (CH$_2$Cl$_2$ and aqueous saturated NaHCO$_3$). The aqueous solution was extracted with CH$_2$Cl$_2$. The combined extracts were washed with brine and dried over Na$_2$SO$_4$. After evaporation, the residue was purified by silica gel chromatography (CH$_2$Cl$_2$:2 M NH$_3$ in MeOH/98:2~93:7) to give the title compound as a 4:1 isomeric mixture (105 mg, 50% yield).

MS (ESI) m/z: 703 (M+H)$^+$.

Step 20b: Compound of Formula V: A and B Taken Together with the Carbon Atom to Which They are Attached are C=CH-phenyl, Q=Ac, and R$_2$'=Ac.

A solution of the compound from Step 20a (105 mg, 0.15 mmol) in CH$_2$Cl$_2$ (3.0 mL) was treated with triethylamine (104 μL, 0.74 mmol) and acetic anhydride (42 μL, 0.45 mmol) at room temperature for 19 hours before evaporation and drying in vacuo to give the title compound.

MS (ESI) m/z: 787 (M+H)$^+$.

Step 20c. Compound of Formula V: A and B Taken Together with the Carbon Atom to Which They are Attached are C=CH-phenyl, Q=Ac and R$_2$'=H.

The title compound is prepared by refluxing the compound from Step 20b in methanol according to the procedure described in Example 1 (Step 1c).

Example 21

Compound of Formula I: A and B Taken Together with the Carbon Atom to Which They are Attached=C=O, X and Y Taken Together with the Carbon Atom to Which They are Attached=C=NAc, L=CH$_2$CH$_3$, W is N(CH$_3$)$_2$, Z=OCH$_2$=CH=CH(quinolin-3-yl), and R$_2$'=H.

Step 21a: Compound of Formula I: A and B Taken Together with the Carbon Atom to Which They are Attached=C=O, X and Y Taken Together with the Carbon Atom to Which They are Attached=C=NH, L=CH$_2$CH$_3$, W is N(CH$_3$)$_2$, Z=OCH$_2$CH=CH(quinolin-3-yl) and R$_2$'=H.

A solution of the title compound from Example 3 (0.5 g, 0.8 mmol) in methanol (5 ml) and dichloromethane (5 ml) was cooled to −78° C. and ozone was bubbled through the reaction until the solution became light blue. Then nitrogen was bubbled through the reaction mixture to remove excess ozone and triphenyl phosphine (1.0 g, 3.8 mmol) was added. The solution was allowed to warm to room temperature over 1 hour. The solvent was evaporated and the residue was dissolved in 20 ml of THF and refluxed overnight. The solvent was removed under vacuum and the residue was purified by flash chromatography (SiO$_2$, CH$_2$Cl$_2$:2M ammonia in methanol=95:5) to give the title compound (0.33 g, 66%)

MS (ESI) m/z 629.2 (M+H)$^+$

Step 21b. Compound of Formula I: A and B Taken Together with the Carbon Atom to Which They are Attached=C=O, X and Y Taken Together with the Carbon Atom to Which They are Attached=C=NAc, L=CH$_2$CH$_3$, W is N(CH$_3$)$_2$, Z=OH and R$_2$'=Ac.

Acetic anhydride (0.17 ml, 1.5 mmol) was added to a solution of the compound from Step 21a (0.3 g, 0.5 mmol)

and triethylamine (0.4 ml, 3.0 mmol) in dichloromethane (10 ml). The reaction mixture was stirred at room temperature for 4 hours, diluted with 100 ml of dichloromethane and washed with saturated sodium bicarbonate (3×100 ml) and brine (100 ml). The organic phase was dried over sodium sulfate and the solvent was removed in vacuo. The residue was purified by silica gel chromatography (hexanes/acetone: 1:1) to give the title compound (0.2 g).

MS (ESI) m/z: 713.1 (M+H)$^+$.

Step 21 c. Compound of Formula I: A and B Taken Together with the Carbon Atom to Which They are Attached=C=O, X and Y Taken Together with the Carbon Atom to Which They are Attached=C=NAc, L=$CH_2CH_3$, Z=$OCH_2CH$=CH(quinolin-3-yl) and $R_2$'=Ac.

A mixture of the compound from Step 21b (55 mg, 0.08 mmol), 3-(t-butoxycarboxy)-3-(3-quinolinyl)-1-propene (60 mg, 0.21 mmol), and 1,4-bis(diphenylphosphino)-butane (10 mg, 0.02 mmol) was dissolved in freshly distilled THF (5.0 ml). To the solution was added $Pd_2(dba)_3$ (12 mg, 0.01 mmol). The reaction mixture was heated to reflux slowly. After refluxing for 14 hours, the reaction was worked up as described in Step 1b of Example 1 and the solid residue was purified by silica gel chromatography (acetone:hexane/1:1) to give the title compound (27 mg).

MS (ESI) m/z 880.3 (M+H)$^+$.

Step 21d: Compound of Formula I: A and B Taken Together with the Carbon Atom to Which They are Attached=C=O, X and Y Taken Together with the Carbon Atom to Which They are Attached=C=NAc, L=$CH_2CH_3$, Z=$OCH_2CH$=CH(quinolin-3-yl) and $R_2$'=H.

The title compound was prepared by refluxing the compound from Step 21c in methanol according to the procedure described in Step 1c of Example 1.

MS (ESI) m/z 838.2 (M+H)$^+$. Selected $^{13}$C NMR: δ 206.0, 184.7, 176.2, 176.1, 149.1, 147.8, 133.0, 129.7, 129.6, 129.5, 128.2, 128.1, 127.8, 127.4, 101.1.

Example 22

Compound of Formula I: A and B Taken Together with the Carbon Atom to Which They are Attached=C=CHCHCH-phenyl, X and Y Taken Together with the Carbon Atom to Which They are Attached=C=NAc, L=$CH_2H_3$, W is $N(CH_3)_2$, Z=OC(O)-benzyl and $R_2$'=H.

Step 22a. Compound of Formula I: A and B Taken Together with the Carbon Atom to Which they are Attached are C=CHCH=CH-phenyl, X and Y Taken Together with the Carbon Atom to Which they are Attached are C=NAc, L=$CH_2CH_3$, W is $N(CH_3)_2$, Z=OH, and $R_2$'=Ac.

To a solution of the compound of formula 1: A and B taken together with the carbon atom to which they are attached are C=$CH_2$, X and Y taken together with the carbon atom to which they are attached are C=NAc, L=$CH_2CH_3$, W is $N(CH_3)_2$, Z =OH, and $R_2$'=Ac (0.5 g, 0.7 mmol) in 8 ml anhydrous DMF, β-bromostyrene (0.15 ml, 1.2 mmol) and $K_2CO_3$ (200 mg, 1.5 mmol) were added at room temperature. The mixture was degassed briefly and a catalytic amount of dihydrogen dichlorobis(di-tert-butylphosphinito-κP)palladate(II) (POPd from Combiphos catalysts, Inc.) was added. The reaction mixture was heated to 100° C. in a sealed tube for 48 hours. Ethyl acetate (50 mL) was added and the solution was washed 3 times with aqueous $NaHCO_3$. The organic layer was dried over anhydrous $Na_2SO_4$. The solvent was evaporated under vacuum and the residue was purified by flash chromatography ($SiO_2$, acetone:hexanes/1:1) to provide the title compound.

MS (ESI) m/z 813 (M+H)$^+$

Step 22b. Compound of Formula I: A and B Taken Together with the Carbon Atom to Which they are Attached are C=CHCH=CH-phenyl, X and Y Taken Together with the Carbon Atom to Which they are Attached are C=NAc. L=$CH_2CH_3$, W is $N(CH_3)_2$, Z=OC(O)$CH_2$(2-pyridyl) and $R_2$'=Ac.

Into a solution of 2-pyridylacetic acid (85.4 mg, 0.48mmol) in $CH_2Cl_2$(1 ml) was added $Et_3N$ (140 µl) at room temperature. Then trimethyl acetic chloride (60 µl, 0.48 mmol) was added to the suspension at 0° C. After stirring at 0° C. for 30 mins, a solution of the compound from Step 22b (100 mg, 0.12 mmol) in $CH_2Cl_2$(1 ml) in pyridine (100 µl) was added at 0° C. The reaction mixture was warmed up to room temperature and stirred for overnight. The mixture was treated with saturated $NaHCO_3$, extracted with ethyl acetate and washed with brine. The organic phase was dried over sodium sulfate and the solvent was removed in vacuo. The crude residue was purified by column chromatography (Aceton/Hexane 1:1) to give the title compound (83 mg).

MS (ESI) m/z: 932 (M+H)$^+$.

Step 22c. Compound of Formula I: A and B Taken Together with the Carbon Atom to Which they are Attached=C=CHCH=CH-phenyl, X and Y Taken Together with the Carbon Atom to Which They are Attached=C=NAc, L=$CH_2CH_3$, W is $N(CH_3)_2$, Z=OC(O)$CH_2$(2-pyridyl) and $R_2$'=H.

The title compound (71 mg) was prepared by stirring the compound from Step 22b in methanol overnight.

MS (ESI) m/z: 890 (M+H)$^+$.

Example 23

Compound of Formula I: Compound of Formula I: A and B Taken Together with the Carbon Atom to Which They are Attached=C=CHCHCH-phenyl, X and Y Taken Together with the Carbon Atom to Which They are Attached=C=NAc, L=$CH_2CH_3$, W is $N(CH_3)_2$, Z=OC(O)$CH_2$(3-pyridyl) and $R_2$'=H.

Step 23a. Compound of Formula I: Compound of Formula I: A and B Taken Together with the Carbon Atom to Which They are Attached=C=CHCH=CH-phenyl, X and Y Taken Together with the Carbon Atom to Which They are Attached=C=NAc, L=$CH_2CH_3$, W is $N(CH_3)_2$, Z=OC(O)$CH_2$(3-pyridyl) and $R_2$'=Ac.

The title compound (59 mg) was prepared with the title compound from step 22a and 3-pyridylacetic acid according to the procedure described in Step22 Step 1c).

MS (ESI) m/z: 932 (M+H)$^+$.

Step 23c. Compound of formula I: A and B Taken Together with the Carbon Atom to Which They are Attached=C=CHCH=CH-phenyl, X and Y Taken Together with the Carbon Atom to Which They are Attached=C=NAc, L=$CH_2CH_3$, W is $N(CH_3)_2$, Z=OC(O)CH(3-pyridyl) and $R_2$'=H The title compound (52 mg) was prepared by stirring the compound from Step 23b in methanol for overnight.

MS (ESI) m/z: 890 (M+H)$^+$.

Example 24

Compound of Formula I: A and B Taken Together with the Carbon Atom to Which They are Attached=C=CH$_2$, X and Y Taken Together with the Carbon Atom to Which They are Attached=C=NOH, L=CH$_2$CH$_3$, W is N(CH$_3$)$_2$, Z=4-oxo-cladinose and R$_2$'=H Step 24a. Compound of Formula IV: A and B Taken Together with the Carbon Atom to Which They are Attached=C=CH$_2$, Q=OH, and R$_2$'=R$_4$"=H.

Into a solution of the compound from Step 22b of example 22 (1 g, 1.07 mmol) in 5 ml methanol was added LiOH(150 mg, 6.25 mmol) at rt. After stirring for overnight the mixture was diluted with ethyl acetate, and washed with saturated NH$_4$Cl and brine. The organic phase was dried over Na$_2$SO$_4$, the solvent was removed in vacuo to give the title compound (0.9 g).

MS (ESI) m/z: 800 (M+H)$^+$.

Step 24b. Compound of Formnula IV: A and B Taken Together with the Carbon Atom to Which They are Attached=C=CH$_2$, Q=OAc, and R$_2$'=Ac, and R$_4$"=H.

Into a solution of the compound from step 24a (1 g, 1.25 mmol) in 2.5 ml CH$_2$Cl$_2$ was added Ac$_2$O (240 ul, 2.5 mmol) and DIEA(870 ul, 5 mmol) at room temperature. After stirring for 1 hour the mixture was diluted with ethyl acetate, and washed with saturated NaHCO$_3$ and brine. The organic phase was dried over Na$_2$SO$_4$, and the solvent removed in vacuo to give the crude title compound (1.2 g).

MS (ESI) m/z: 885 (M+H)$^+$.

Step 24c. Compound of Formula I: A and B Taken Together with the Carbon Atom to Which They are Attached=C=CH$_2$, X and Y Taken Together with the Carbon Atom to Which They are Attached=C=NOAc, L=CH$_2$CH$_3$, W is N(CH$_3$)$_2$, Z=4-oxocladinose and R$_2$'=Ac.

Into a solution of the crude compound from step 24b in 7 ml of CH$_2$Cl$_2$ was added DMSO (1.3 ml, 18.75 mmol) and EDC-HCl (1.2 g, 6.25 mmol) at 0° C. Then Py-TFA (1.2 g, 6.25 mmol) was added at 0° C. The mixture was warmed to room temperature and stirred overnight. The mixture was diluted with ethyl acetate, and washed with saturated NaHCO$_3$ and brine. The organic phase was dried over Na$_2$SO$_4$, the solvent removed in vacuo and the solid residue was purified by silica gel chromatography (acetone:hexane/1:1) to give the title compound (890 mg).

MS (ESI) m/z: 883 (M+H)$^+$.

Step 24d. Compound of Formula I: A and B Taken Together with the Carbon Atom to Which They are Attached=C=CH$_2$, X and Y Taken Together with the Carbon Atom to Which They are Attached=C=NOH, L=CH$_2$CH$_3$, W is N(CH$_3$)$_2$, Z=4-oxocladinose and R$_2$'=H.

A solution of the compound from Step 24c (50 mg) in 2 ml methanol was heated at 55° C. for 48 hours. The solvent was removed in vacuo and the compound was purified by column chromatography (CH$_2$Cl$_2$: 2M ammonia in MeOH/97:3) to give the title compound (20 mg).

MS (ESI) m/z: 799 (M+H)$^+$.

Example 25

Compound of Formula I: A and B Taken Together with the Carbon Atom to Which They are Attached=C=CH$_2$, X and Y Taken Together with the Carbon Atom to Which They are Attached=C=NOH, L=CH$_2$CH$_3$, W is N(CH$_3$)$_2$, Z=4-oximecladinose and R$_2$'=H.

Into a solution of the compound from Step 24c of Example 24 (840 mg, 0.95 mmol) in 4 ml of 2-PrOH was added H$_2$NOH—HCl (140 mg, 1.9 mmol) at room temperature followed by the addition of Et$_3$N (260 ul, 1.9 mmol). The mixture was stirred at room temperature for 2 hours and heated at 45° C. for 20 minutes. Then acetic acid (108 ul) was added and the mixture heated at 40° C. overnight. Another 70 mg of H$_2$NOH—HCl was added and the mixture heated at 45° C. for 6 hourrs. The mixture was diluted with ethyl acetate, and washed with saturated NaHCO$_3$ and brine. The organic phase was dried over Na$_2$SO$_4$, the solvent removed in vacuo and the solid residue was purified by silica gel chromatography (CH$_2$Cl$_2$: 2M ammonia in MeOH/97:3) to give the title compound (400 mg).

MS (ESI) m/z: 814 (M+H)$^+$.

Example 26

Compound of Formula IV: A and B Taken Together with the Carbon Atom to Which They are Attached are C=CH$_2$, Q=OH, and R$_2$'=R$_4$"=H.

A solution of the compound from Step 24b of example 24 (50 mg) in 2 ml methanol was heated at room temperature for 48 hours. The solvent was removed in vacuo and the compound was purified by column chromatography (CH$_2$Cl$_2$: 2M ammonia in MeOH/97:4) to give the title compound (23 mg).

MS (ESI) m/z: 801 (M+H)$^+$.

Example 27

Compound of Formula I: Compound of Formula IV: A and B Taken Together with the Carbon Atom to Which They are Attached=C=CH2, Q=OH, R$_2$'=H, and R$_4$"=Ac.

Step 27a. Compound of Formula IV: A and B Taken Together with the Carbon Atom to Which They are Attached=C=CH, Q=OCH$_3$, R$_2$'=Ac, and R$_4$"=Ac.

A mixture of the compound from Step 5a of Example 5 (100 mg, 0.11 mmol) and NaH (60% in mineral oil, 7 mg, 0.17 mmol) in 0.5 ml DMF was stirred at room temperature for one minute before methyl iodide (0.007 mL, 0.11 mmol) was added. After 15 minutes the mixture was quenched with water. The mixture was extracted with hexanes-ether (1:1). The extracts were dried over Na$_2$SO$_4$ and the solvent was removed in vacuo to give the crude title compound (80 mg).

MS (ESI) m/z: 899 (M+H)$^+$.

Step 27b. Compound of Formula IV: A and B Taken Together with the Carbon Atom to Which They are Attached=C=CH$_2$, Q=OCH$_3$, R$_2$'=H, and R$_4$"=H.

The title compound (40 mg) was prepared by stirring the compound from Step 27a (80 mg) in methanol at room temperature for 16 hours and refluxing for 2 hours according to the procedure described in Example 1 (Step 1c).

MS (ESI) m/z: 857 (M+H)$^+$.

Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed is:

1. A compound represented by the formula

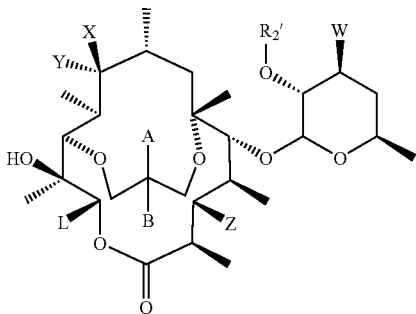

(I)

as well as its pharmaceutically acceptable salts, esters and prodrugs, wherein

A is:
a) —$OR_p$, where $R_p$ is a hydroxy protecting group;
b) —$R_1$, where $R_1$ is independently:
 (1) aryl;
 (2) substituted aryl;
 (3) heteroaryl; or
 (4) substituted heteroaryl;
c) —$OR_1$;
d) —$R_2$, where $R_2$ is:
 (1) hydrogen;
 (2) halogen;
 (3) $C_1$–$C_{12}$ alkyl optionally containing 0, 1, 2, or 3 heteroatoms selected from the group consisting of O, S or N, optionally substituted with one or more substituents selected from the group consisting of halogen, aryl, substituted aryl, heteroaryl, and substituted heteroaryl;
 (4) $C_2$–$C_{12}$ alkenyl optionally containing 0, 1, 2, or 3 heteroatoms selected from the group consisting of O, S and N, optionally substituted with one or more substituents selected from the group consisting of halogen, aryl, substituted aryl, heteroaryl, and substituted heteroaryl; and
 (5) $C_2$–$C_{12}$ alkynyl optionally containing 0, 1, 2, or 3 heteroatoms selected from the group consisting of O, S and N, optionally substituted with one or more substituents selected from the group consisting of halogen, aryl, substituted aryl, heteroaryl, and substituted heteroaryl;
e) —$OR_2$;
f) —$S(O)_nR_{11}$, where n=0, 1 or 2, and $R_{11}$ is independently hydrogen, $R_1$ or $R_2$;
g) —$NHC(O)R_{11}$;
h) —$NHC(O)NHR_{11}$;
i) —$NHS(O)_2R_{11}$;
j) $NR_{14}R_{15}$, where $R_{14}$ and $R_{15}$ are each independently $R_{11}$; or
k) —$NHR_3$, where $R_3$ is an amino protecting group;

B is:
a) hydrogen;
b) deuterium;
c) halogen;
d) —OH;
e) $R_1$;
f) $R_2$; or
g) —$OR_p$;

h) provided that when B is halogen, —OH, or —$OR_p$, A is $R_1$ or $R_2$;

or alternatively, A and B taken together with the carbon atom to which they are attached are:
a) C=O;
b) $C(OR_2)_2$;
c) $C(SR_2)_2$;
d) $C(OR_{12})(OR_{13})$, where $R_{12}$ and $R_{13}$ are independently $C_1$–$C_6$ alkyl or taken together are —$(CH_2)_m$—, where m=2 or 3;
e) $C(SR_{12})(SR_{13})$;
f) C=$CHR_{11}$;
g) C=N—O—$R_{11}$;
h) C=N—O—$Ar_1$—M—$Ar_2$, wherein
 (1) —$Ar_1$— is $R_{31}$, where $R_{31}$ is independently selected from:
  (a) —$R_1$;
  (b) —$C_1$–$C_{12}$ alkyl optionally containing 0, 1, 2, or 3 heteroatoms selected from the group consisting of O, S or N, optionally substituted with one or more substituents selected from the group consisting of halogen, aryl, substituted aryl, heteroaryl, and substituted heteroaryl;
  (c) —$C_2$–$C_{12}$ alkenyl optionally containing 0, 1, 2, or 3 heteroatoms selected from the group consisting of O, S and N, optionally substituted with one or more substituents selected from the group consisting of halogen, aryl, substituted aryl, heteroaryl, and substituted heteroaryl; or
  (d) —$C_2$–$C_{12}$ alkynyl optionally containing 0, 1, 2, or 3 heteroatoms selected from the group consisting of O, S and N, optionally substituted with one or more substituents selected from the group consisting of halogen, aryl, substituted aryl, heteroaryl, and substituted heteroaryl;
 (2) -M- is absent or selected from the group consisting of:
  (a) —$C_1$–$C_{12}$ alkyl optionally containing:
   1. 0–3 heteroatoms selected from the group consisting of O, S and N; and
   2. 0–3 groups selected from the group consisting of —C=N—, —N=N— and C(O);
  (b) —$C_2$–$C_{12}$ alkenyl optionally containing:
   1. 0–3 heteroatoms selected from the group consisting of O, S and N; and
   2. 0–3 groups selected from the group consisting of —C=N—, —N=N—, and C(O);
  (c) —$C_2$–$C_{12}$ alkynyl optionally containing;
   1. 0–3 heteroatoms selected from the group consisting of O, S and N; and
   2. 0–3 groups selected from the groups consisting of —C=N—, —N=N—, and C(O);
  (d) substituted aryl;
  (e) substituted heteroaryl; and
  (f) substituted heterocycloalkyl; and
 (3) -$Ar_2$ is:
  (a) aryl;
  (b) substituted aryl;
  (c) heteroaryl; or
  (d) substituted heteroaryl;
i) C=$NNHR_{11}$;
j) C=$NNHC(O)R_{11}$;
k) C=$NNHC(O)NHR_{11}$;
l) C=$NNHS(O)_2R_{11}$;
m) C=$NNHR_3$;
n) C=$NR_{11}$;
o) C=N—N—$CHR_{11}$; and one of X and Y is hydrogen and the other is:
a) hydrogen;
b) deuterium;
c) —OH;
d) —OR$_p$;
e) —NR$_4$R$_5$, where R$_4$ and R$_5$ are each independently:
(1) hydrogen;
(2) C$_1$–C$_{12}$ alkyl, optionally substituted with one or more substituents selected from the group consisting of halogen, aryl, substituted aryl, heteroaryl and substituted heteroaryl; or
(3) R$_4$ and R$_5$, taken together with the nitrogen atom to which they are attached form a 3–10 membered heteroalkyl ring containing 0–2 additional hetero atoms selected from the group consisting of O, S and N; or alternatively, X and Y taken together with the carbon atom to which they are attached are:
a) C=O;
b) C=NQ, wherein Q is:
(1) R$_{11}$;
(2) amino protecting group;
(3) C(O)R$_{11}$; or
(4) OR$_6$, where R$_6$ is independently:
  (a) hydrogen;
  (b) —CH$_2$O(CH$_2$)$_2$OCH$_3$,
  (c) —CH$_2$O(CH$_2$O)$_n$CH$_3$;
  (d) —C$_1$–C$_{12}$ alkyl, optionally substituted with one or more substituents selected from the group consisting of aryl, substituted aryl, heteroaryl and substituted heteroaryl;
  (e) C$_3$–C$_{12}$ cycloalkyl;
  (f) C(O)—C$_1$–C$_{12}$ alkyl;
  (g) C(O)—C$_3$–C$_{12}$ cycloalkyl;
  (h) C(O)—R$_{11}$; or
  (i) —Si(R$_a$)(R$_b$)(R$_c$), wherein R$_a$, R$_b$ and R$_c$ are each independently C$_1$–C$_{12}$ alkyl, aryl or substituted aryl; or
(5) O—C(R$_7$)(R$_8$)—O—R$_6$, provided that R$_6$ is not C(O)—C$_1$–C$_{12}$ alkyl, C(O)—C$_3$–C$_{12}$ cycloalkyl, or C(O)—R$_1$, and R$_7$ and R$_8$ taken together with the carbon atom to which they are attached form a C$_3$–C$_{12}$ cycloalkyl group or each independently is:
  1. hydrogen; or
  2. C$_1$–C$_{12}$ alkyl;

L is:
a) —CH(OH)CH$_3$;
b) C$_1$–C$_6$ alkyl, optionally substituted with one or more substituents selected from the group consisting of aryl, substituted aryl, heteroaryl, and substituted heteroaryl;
c) C$_2$–C$_6$ alkenyl, optionally substituted with one or more substituents selected from the group consisting of aryl, substituted aryl, heteroaryl, and substituted heteroaryl; or
d) C$_2$–C$_6$ alkynyl, optionally substituted with one or more substituents selected from the group consisting of aryl, substituted aryl, heteroaryl, and substituted heteroaryl;

W is —NR$_{14}$R$_{15}$, where R$_{14}$ and R$_{15}$ are each independently:
a) hydrogen;
b) C$_1$–C$_{12}$ alkyl, optionally substituted with one or more substituents selected from the group consisting of halogen, aryl, substituted aryl, heteroaryl and substituted heteroaryl;
c) C$_1$–C$_{12}$ alkenyl, optionally substituted with one or more substituents selected from the group consisting of halogen, aryl, substituted aryl, heteroaryl and substituted heteroaryl;
d) C$_1$–C$_{12}$ alkynyl, optionally substituted with one or more substituents selected from the group consisting of halogen, aryl, substituted aryl, heteroaryl and substituted heteroaryl; or
e) R$_{14}$ and R$_{15}$, taken together with the nitrogen atom to which they are attached form a heterocycloalkyl moiety;

Z is:
a) hydrogen;
b) —OR$_p$;
c) —OR$_{11}$;
d) —OC(O)R$_{11}$;
e) —OC(O)NHR$_{11}$;
f) —S(O)$_n$R$_{11}$; or
g) —

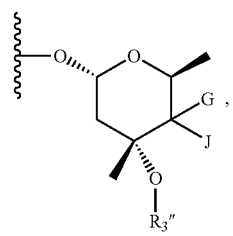

where
i. R$_3$" is hydrogen or methyl; and
ii. where one of J or G is hydrogen, the other is selected from:
  1. hydrogen;
  2. deuterium;
  3. —OR$_4$", where R$_4$" is hydrogen or R$_p$; or
  4. —NR$_4$R$_5$; or
iii. in the alternative, J and G are taken together with the carbon atom to which they are attached form a group selected from the group consisting of:
  1. C=O; and
  2. C=N—Q; and R$_2$' is hydrogen or R$_p$.

2. A compound according to claim 1, which is represented by formula II:

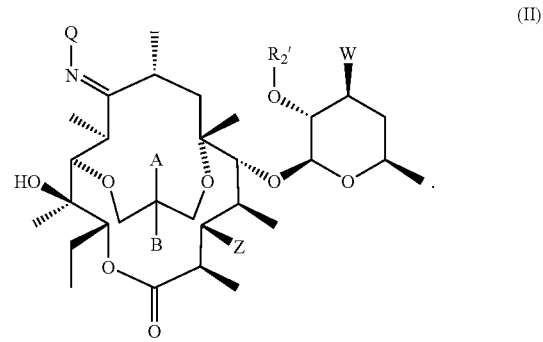

(II)

3. A compound according to claim 1, which is represented by formula III:

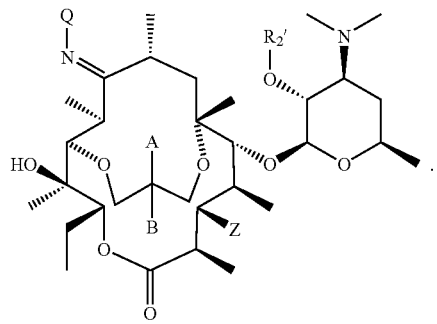

(III)

4. A compound according to claim 1, which is represented by formula IV:

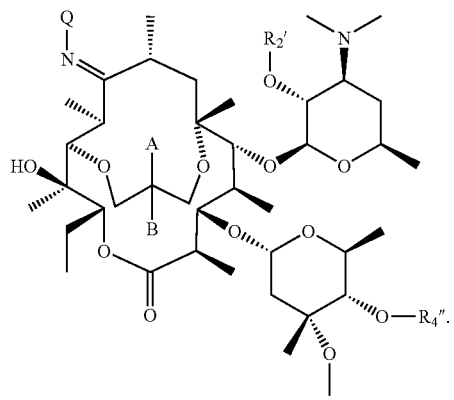

(IV)

5. A compound according to claim 1, which is represented by formula V:

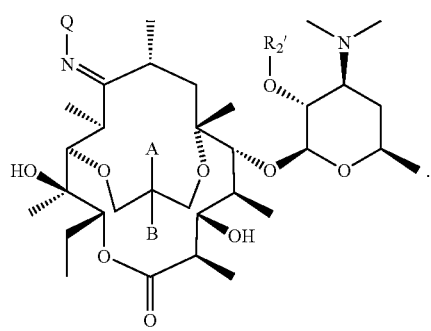

(V)

6. A compound according to claim 1, which is represented by formula VI:

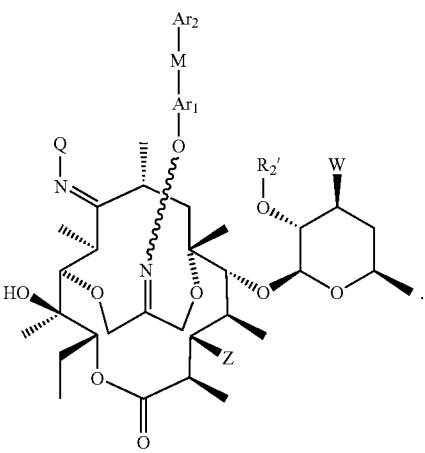

(VI)

7. A compound according to claim 1, which is represented by formula VII:

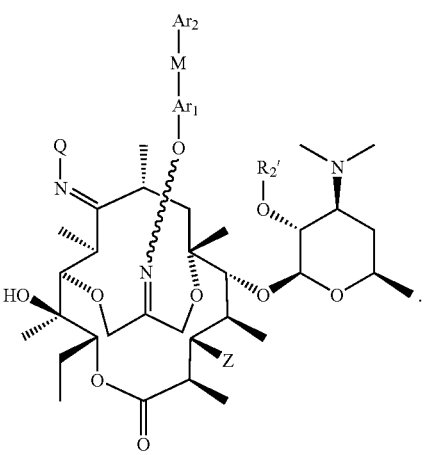

(VII)

8. A compound according to claim 1, which is represented by formula VIII:

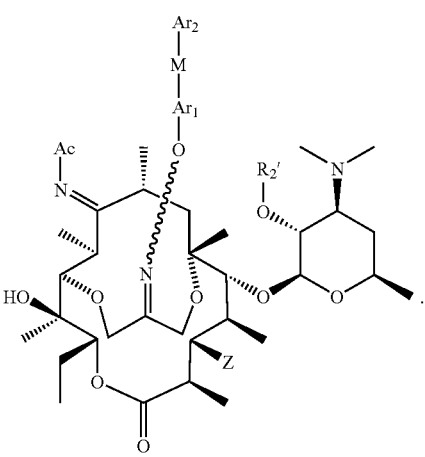

(VIII)

9. A compound according to claim 1, which is represented by formula IX:

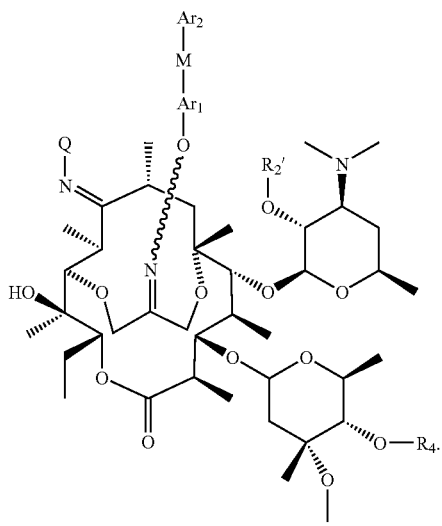

(IX)

10. A compound according to claim 1, which is represented by formula X:

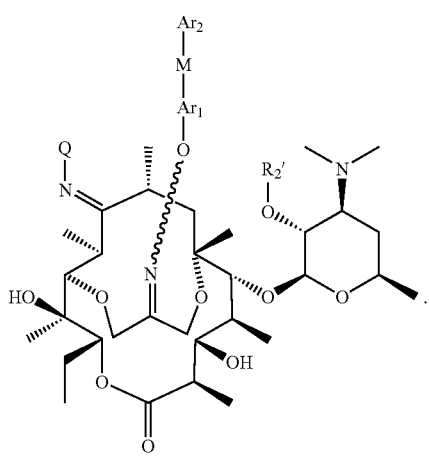

(X)

11. A compound according to claims 1, 4, or 5 which is selected from the group consisting of:

Compound of formula IV: A and B taken together with the carbon atom to which they are attached=C═CH$_2$, Q=OH, R$_2$' is H, and R$_4$"=Ac;

Compound of formula IV: A and B taken together with the carbon atom to which are attached=C═CH$_2$, Q=H, R$_2$'=H, and R$_4$"=Ac;

Compound of formula V: A and B taken together with the carbon atom to which they are attached=C═CH$_2$, Q=H, and R$_2$'=H;

Compound of formula V: A and B taken together with the carbon atom to which they are attached=C═CH$_2$, Q=Ac, and R$_2$'=H;

Compound of formula IV: A and B taken together with the carbon atom to which they are attached=C═CH$_2$, Q=O—CH$_2$OCH$_3$, R$_2$'=H, and R$_4$"=Ac;

Compound of formula V: A and B taken together with the carbon atom to which they are attached=C═CH$_2$, Q=O—CH$_2$OCH$_3$, and R$_2$'=H;

Compound of formula I: A and B taken together with the carbon atom to which they are attached=C═CH$_2$, X and Y taken together with the carbon atom to which they are attached=C═NAc, L=CH$_2$CH$_3$, W is N(CH$_3$)$_2$, Z=H and R$_2$'=H;

Compound of formula I: A and B taken together with the carbon atom to which they are attached=C═CH$_2$, X and Y taken together with the carbon atom to which they are attached=C═NAc, L=CH$_2$CH$_3$, Z=OC(O)(p-nitrophenyl) and R$_2$'=H;

Compound of formula I: A and B taken together with the carbon atom to which they are attached=C═CH$_2$, X and Y taken together with the carbon atom to which they are attached=C═NAc, L=CH$_2$CH$_3$, W is N(CH$_3$)$_2$, Z=OC(O)[2-(NO$_2$), 4-(CF$_3$)Phenyl] and R$_2$'=H;

Compound of formula I: A and B taken together with the carbon atom to which they are attached=C═CH$_2$, X and Y taken together with the carbon atom to which they are attached=C═NAc, L=CH$_2$CH$_3$, W is N(CH$_3$)$_2$, Z=OC(O)CH$_2$(p-methoxyphenyl) and R$_2$'=H;

Compound of formula IV: A and B taken together with the carbon atom to which they are attached=C═CH$_2$, Q=Ac, R$_2$'=H, and R$_4$"=Ac;

Compound of formula I: Compound of formula IV: A and B taken together with the carbon atom to which they are attached=C═O, Q=Ac, R$_2$'=H, and R$_4$"=Ac;

Compound of formula IV: A and B taken together with the carbon atom to which they are attached=C═OBz, Q=Ac, R$_2$'=H, and R$_4$"=Ac;

Compound of formula IV: A and B taken together with the carbon atom to which they are attached=C═CH-(3-quinolyl), Q=Ac, R$_2$'=H, and R$_4$"=Ac;

Compound of formula I: A and B taken together with the carbon atom to which they are attached=C═CH$_2$, X and Y taken together with the carbon atom to which they are attached=C═O, L=CH$_2$CH$_3$, W is N(CH$_3$)$_2$, Z=4-acetoxycladinose and R$_2$'=H;

Compound of formula I: A and B taken together with the carbon atom to which they are attached=C═CH-quinolin-3-yl, X and Y taken together with the carbon atom to which they are attached=C═O, L=CH$_2$CH$_3$, W is N(CH$_3$)$_2$, Z=4-acetoxycladinose and R$_2$'=H;

Compound of formula I: A and B taken together with the carbon atom to which they are attached=C═CH-quinolin-3-yl, X and Y taken together with the carbon atom to which they are attached=C═O, L=CH$_2$CH$_3$, W is N(CH$_3$)$_2$, Z=OH, and R$_2$'=H;

Compound of formula I: A and B taken together with the carbon atom to which they are attached=C═CH$_2$, X and Y taken together with the carbon atom to which they are attached=C═O, L=CH$_2$CH$_3$, W is N(CH$_3$)$_2$, Z=OH and R$_2$'=H;

Compound of formula IV: A and B taken together with the carbon atom to which they are attached=C═CH$_2$-phenyl, Q=OH, R$_2$'=H, and R$_4$"=Ac;

Compound of formula V: A and B taken together with the carbon atom to which they are attached are C=CH-phenyl, Q=Ac, and R$_2$'=H;

Compound of formula I: A and B taken together with the carbon atom to which they are attached=C=O, X and Y taken together with the carbon atom to which they are attached=C=NAc, L=CH$_2$CH$_3$, W is N(CH$_3$)$_2$, Z=OCH$_2$CH=CH(quinolin-3-yl), and R$_2$'=H;

Compound of formula I: A and B taken together with the carbon atom to which they are attached=C=CHCHCH-phenyl, X and Y taken together with the carbon atom to which they are attached=C=NAc, L=CH$_2$CH$_3$, W is N(CH$_3$)$_2$, Z=OC(O)-benzyl and R$_2$'=H;

Compound of formula I: A and B taken together with the carbon atom to which they are attached=C=CHCHCH-phenyl, X and Y taken together with the carbon atom to which they are attached=C=NAc, L=CH$_2$CH$_3$, W is N(CH$_3$)$_2$, Z=OC(O)CH$_2$(2-pyridyl) and R$_2$'=H;

Compound of formula I: A and B taken together with the carbon atom to which they are attached=C=CH$_2$, X and Y taken together with the carbon atom to which they are attached=C=NOH, L=CH$_2$CH$_3$, W is N(CH$_3$)$_2$, Z=4-oxocladinose and R$_2$'=H;

Compound of formula I: A and B taken together with the carbon atom to which they are attached=C=CH$_2$, X and Y taken together with the carbon atom to which they are attached=C=NOH, L=CH$_2$CH$_3$, W is N(CH$_3$)$_2$, Z=4-oximecladinose and R$_2$'=H;

Compound of formula IV: A and B taken together with the carbon atom to which they are attached are C=CH$_2$, Q=OH, and R$_2$'=R$_4$"=H; or Compound of formula I: Compound of formula IV: A and B taken together with the carbon atom to which they are attached=C=CH$_2$, Q=OH, R$_2$'=H, and R$_4$"=Ac.

12. A pharmaceutical composition comprising a therapeutically effective amount of a compound of claim 1, or a pharmaceutically-acceptable salt, ester or prodrug thereof, in combination with a pharmaceutically acceptable carrier.

13. A method for treating a bacterial infection in a subject in need of such comprising administering to an animal a therapeutically-effective amount of a pharmaceutical composition according to claim 12.

14. A process for preparing a compound according to claim 1 represented by the formula:

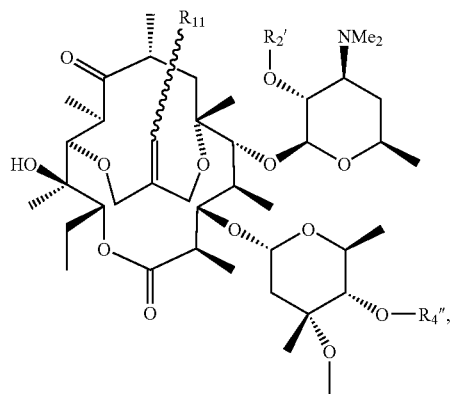

comprising:

(a) reacting a compound represented by the formula

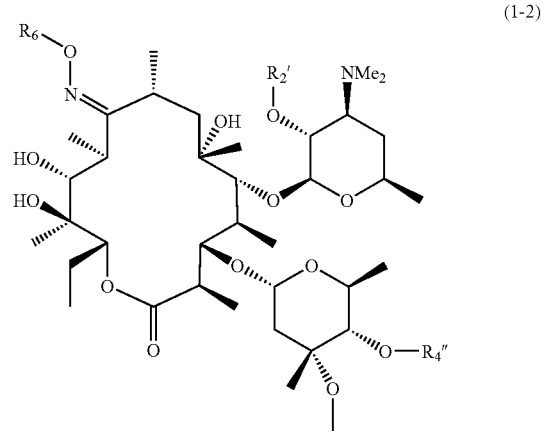

(1-2)

with an alkylating agent represented by the formula

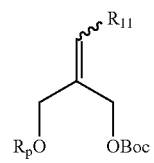

(7-1)

in the presence of a palladium catalyst to provide a compound represented by the formula

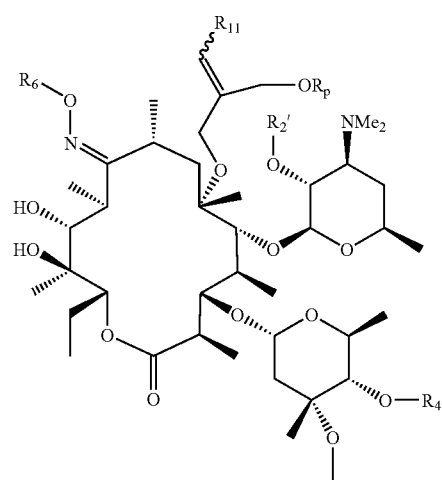

(7-2)

(b) deprotecting the compound from step (a) by reaction with a base to provide a compound represented by the formula

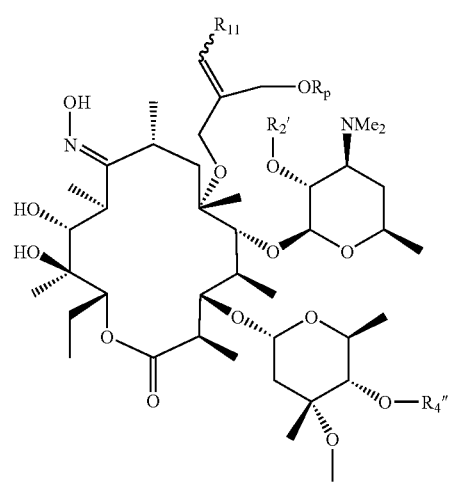

(7-3)

(c) reacting the compound from step (b) with a sulfite reducing agent or TiCl$_3$ to provide a compound represented by the formula

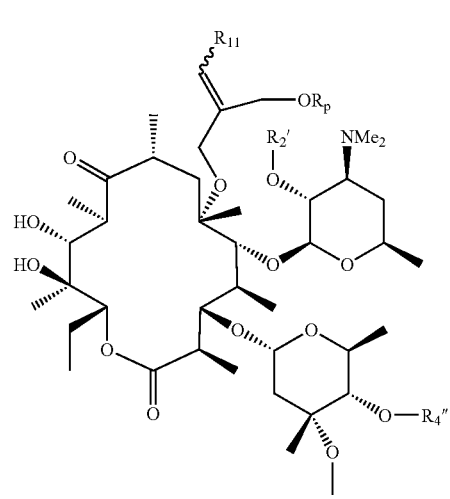

(7-4)

(d) reacting the compound from step (c) to provide a compound represented by the formula

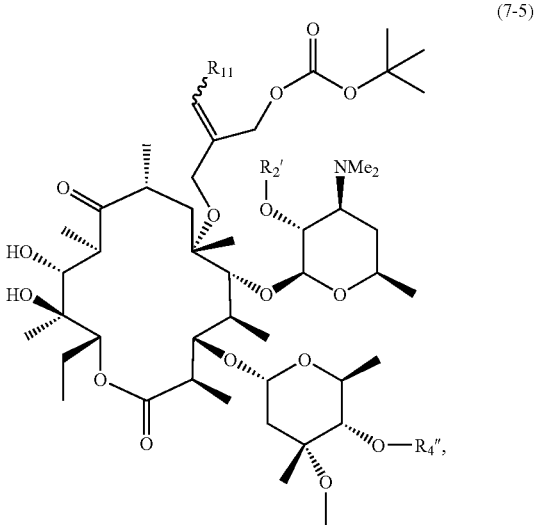

(7-5)

and (e) cyclizing the compound from step (d) using palladium catalyst.

15. A process for the preparation of a compound according to claim 1 represented by the formula (IX):

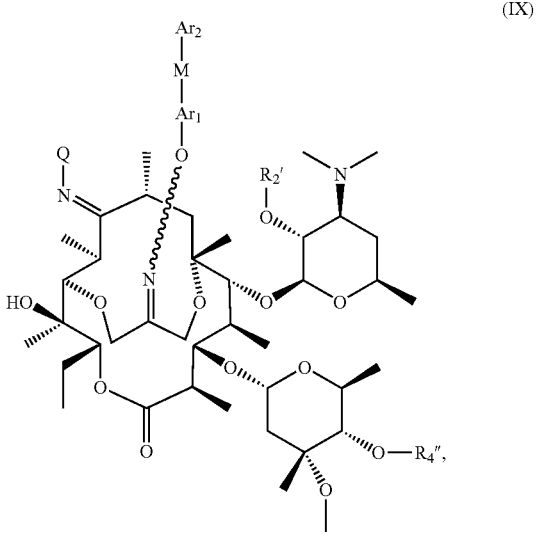

(IX)

comprising the steps of:
(a) reacting a compound represented by the formula (16a)

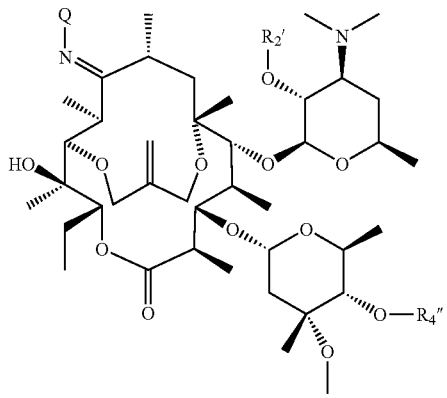

(16a)

with a reagent or reagents capable of performing oxidative cleavage;
(b) reacting a compound from step (a) represented by the formula (16b)

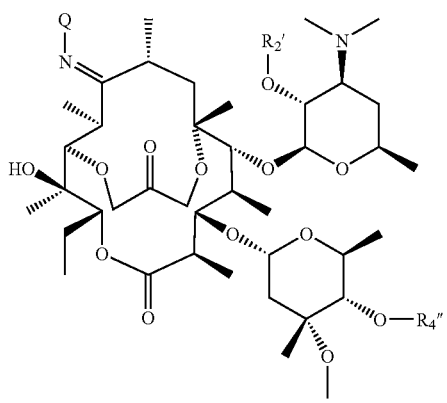

(16b)

with a compound of the formula $Ar_1$-M-$Ar_2$-O—$NH_2$ in the presence of an acid or a base; and
(c) optionally deprotecting the compound from step (d).

16. A compound according to claim 1 of formula I, wherein A and B taken together with the carbon to which they are attached are C=$CH_2$.

17. A compound according to claim 1 of formula I, wherein A and B taken together with the carbon to which they are attached are C=$CH_2$ and Z is

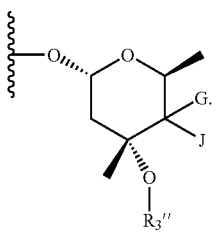

18. A compound according to claim 1 of formula I, wherein A and B taken together with the carbon to which they are attached are C=$CH_2$, L is ethyl, X and Y taken together with the carbon to which they are attached are C=N—Ac, W is $N(CH_3)_2$, $R_2'$ is Ac, and Z is

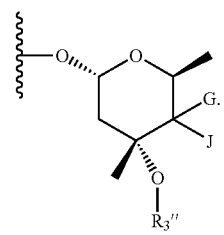

19. A compound according to claim 1 of formula I, wherein A and B taken together with the carbon to which they are attached are C=$CH_2$, L is ethyl, X and Y taken together with the carbon to which they are attached are C=NH, W is $N(CH_3)_2$, $R_2$ is Ac, and Z is OH.

20. A compound according to claim 1 of formula I, wherein A and B taken together with the carbon to which they are attached are C=$CH_2$, L is ethyl, X and Y taken together with the carbon to which they are attached are C=NH, W is $N(CH_3)_2$, $R_2'$ is H, and Z is OH.

21. A compound according to claim 1 of formula I, wherein A and B taken together with the carbon to which they are attached are C=$CH_2$, L is ethyl, X and Y taken together with the carbon to which they are attached are C=N—Ac, W is $N(CH_3)_2$, $R_2'$ is Ac, and Z is OH.

22. A compound according to claim 1 of formula I, wherein A and B taken together with the carbon to which they are attached are C=$CH_2$, L is ethyl, X and Y taken together with the carbon to which they are attached are C=N—Ac, W is $N(CH_3)_2$, $R_2'$ is hydrogen, and Z is OH.

23. A compound according to claim 1 of formula I, wherein A and B taken together with the carbon to which they are attached are C=O.

24. A compound according to claim 1 of formula I, wherein A and B taken together with the carbon to which they are attached are C=O and Z is

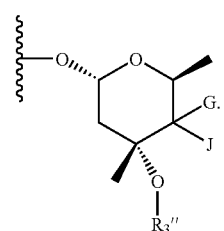

25. A compound according to claim 1 of formula I, wherein A and B taken together with the carbon to which they are attached are C=O, L is ethyl, X and Y taken together with the carbon to which they are attached are C=N—Ac, W is N(CH$_3$)$_2$, and Z is

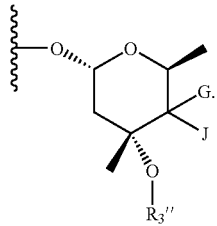

26. A compound according to claim 1 of formula I, wherein A and B taken together with the carbon to which they are attached are C=O L is ethyl, X and Y taken together with the carbon to which they are attached are C=N—Ac, W is N(CH$_3$)$_2$, R$_2$' is Ac, and Z is OH.

27. A process for preparing a compound according to claim 1 of formula I, wherein A and B are taken together with the carbon to which they are attached are C=CHR$_{11}$, X and Y taken together with the carbon to which they are attached are C=N-Q, and Z is

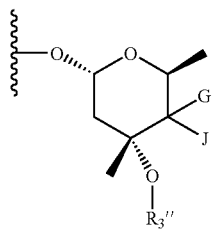

comprising the step of:
a) providing a compound represented by the following formula:

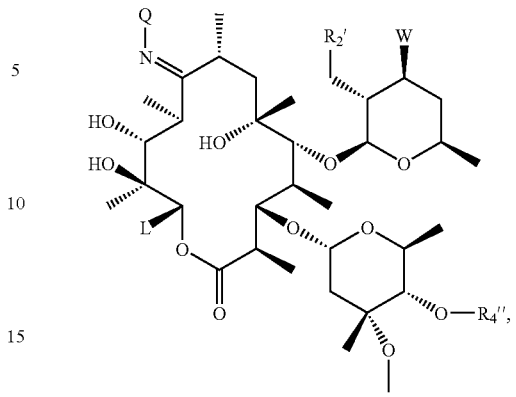

and b) reacting said compound with a compound of R$_{12}$—OC(O)—CH$_2$[C=CHR$_{11}$]CH$_2$—OC(O)—R$_{12}$, wherein R$_{12}$ is independently C$_1$–C$_6$ alkyl and R$_{11}$ is as defined in claim 1.

28. A process according to claim 27, wherein R$_{11}$ is hydrogen.

29. A process according to claim 27, wherein R$_{12}$ is tert-butyl.

30. A process according to claim 27, wherein R$_p$ is Ac.

31. A process according to claim 27, wherein Q is OAc.

32. A process according to claim 27, wherein R$_{11}$ is hydrogen, L is ethyl, Q is OAc, W is N(CH$_3$)$_2$, and R$_2$'=R$_4$''=hydrogen.

33. A process according to claim 27, wherein said palladium catalyst is a palladium (0) catalyst.

34. A process according to claim 27, wherein the reacting is carried out in an aprotic solvent.

35. A process according to claim 34, wherein said aprotic solvent is tetrahydrofuran.

* * * * *